US010624727B2

(12) United States Patent
Sufyan et al.

(10) Patent No.: US 10,624,727 B2
(45) Date of Patent: Apr. 21, 2020

(54) MEDICAL IMPLANTS AND FABRICATION OF MEDICAL IMPLANTS

(71) Applicant: IPENGINE MANAGEMENT (INDIA) PRIVATE LIMITED, New Delhi (IN)

(72) Inventors: Mohammad Sufyan, New Delhi (IN); Rajeev Malhotra, Newton, MA (US)

(73) Assignee: IPENGINE MANAGEMENT (INDIA) PRIVATE LIMITED, New Delhi (IN)

( * ) Notice: Subject to any disclaimer, the term of this patent is extended or adjusted under 35 U.S.C. 154(b) by 248 days.

(21) Appl. No.: 15/322,162

(22) PCT Filed: Jun. 25, 2015

(86) PCT No.: PCT/IN2015/050051
§ 371 (c)(1),
(2) Date: Dec. 26, 2016

(87) PCT Pub. No.: WO2015/198352
PCT Pub. Date: Dec. 30, 2015

(65) Prior Publication Data
US 2017/0128184 A1   May 11, 2017

(30) Foreign Application Priority Data

Jun. 26, 2014   (IN) .......................... 1715/DEL/2014

(51) Int. Cl.
*A61F 2/00*   (2006.01)
*A61B 5/20*   (2006.01)
(Continued)

(52) U.S. Cl.
CPC ............ *A61F 2/0045* (2013.01); *A61B 5/205* (2013.01); *A61F 2/0027* (2013.01);
(Continued)

(58) Field of Classification Search
CPC .... A61F 2/0031; A61F 2/0036; A61F 2/0045; A61F 2/0063; A61F 2002/0068;
(Continued)

(56) References Cited

U.S. PATENT DOCUMENTS

2002/0010457 A1*   1/2002   Duchon ................ A61F 2/0063
                                                      604/515
2014/0275754 A1*   9/2014   Pereira ................. A61F 2/0045
                                                      600/37

* cited by examiner

*Primary Examiner* — Thaddeus B Cox
(74) *Attorney, Agent, or Firm* — Sheets Law Office; Kendal Sheets

(57) ABSTRACT

The present invention discloses a biomechanically compatible implant, wherein arbitrary selectable discrete locations of the implant are defined to exhibit biomechanical characteristics in accordance with biomechanical characteristics at arbitrary selectable discrete locations of a bodily tissue where the respective arbitrary selectable discrete locations of the implant are configured to be attached. The implant may be configured to repair prolapse in an embodiment. In another embodiment, the implant may be configured to repair urinary incontinence. The present invention further discloses a device for generating a biomechanical characteristics pattern of the bodily tissue and the implant. The present invention further discloses a system for designing and fabricating the biomechanically compatible implant.

12 Claims, 18 Drawing Sheets

(51) Int. Cl.
*A61B 17/34* (2006.01)
*A61N 1/05* (2006.01)
*A61N 1/36* (2006.01)

(52) U.S. Cl.
CPC ..... *A61B 17/3468* (2013.01); *A61F 2230/006* (2013.01); *A61F 2240/002* (2013.01); *A61F 2250/0018* (2013.01); *A61F 2250/0023* (2013.01); *A61N 1/0514* (2013.01); *A61N 1/36007* (2013.01)

(58) Field of Classification Search
CPC .......................... A61F 2250/0014–0018; A61F 2250/0023–0029; A61F 2240/002
See application file for complete search history.

MEDICAL IMPLANTS AND FABRICATION OF MEDICAL IMPLANTS

BACKGROUND

Field

The present invention generally relates to medical devices and more particularly relates to medical implants, surgical procedures of delivering the medical implants in a patient's body, and methods and systems for designing and fabricating these medical implants.

Description of the Related Art

Biomechanical properties of bodily tissues such as elasticity, viscoelasticity, resistance to creep, etc may be different at different locations or may vary along different directions due to anisotropic nature of the bodily tissues. For example, vaginal wall properties differ along different portions and in different directions. Even biomechanical properties of the same wall such as anterior vaginal wall or posterior vaginal wall may be different at different locations of the same wall. Further, biomechanical properties of anterior wall and posterior wall are different from one another. Still, same tissues of different patients such as same portions of the same vaginal wall may behave differently biomechanically.

There is a need for a patient-specific customized implant that exhibits biomechanical properties and behaves biomechanically in accordance with the biomechanical properties of the bodily tissues. There is still a need for a device and system that is capable of designing and fabricating such a patient-specific customized implant used for reconstruction of tissues, hernia repair, prolapse repair, incontinence repair or for any other purpose in accordance with the varying properties of the bodily tissues.

SUMMARY

The present invention provides a biomechanically compatible implant for providing support to vaginal walls to treat vaginal walls prolapse in an embodiment. The biomechanically compatible implant includes a first flap configured to be attached to an anterior vaginal wall, wherein arbitrary selectable discrete locations of the first flap of the implant are defined to exhibit biomechanical characteristics in accordance with biomechanical characteristics at arbitrary selectable discrete locations of the anterior vaginal wall where the respective arbitrary selectable discrete locations of the first flap are configured to be attached. The biomechanically compatible implant further includes a second flap configured to be attached to a posterior vaginal wall, wherein arbitrary selectable discrete locations of the second flap of the implant are defined to exhibit biomechanical characteristics in accordance with biomechanical characteristics at arbitrary selectable discrete locations of the posterior vaginal wall where the respective arbitrary selectable discrete locations of the second flap are configured to be attached. The biomechanically compatible implant further includes a third flap extending from the first flap and the second flap and configured to be attached to a tissue proximate sacrum.

The present invention provides a biomechanically compatible implant for providing support to sub-urethral or bladder neck tissues to prevent leakage of urine due to incontinence in an embodiment. The biomechanically compatible implant includes a linear strip of mesh with a proximal portion, a medial portion and a distal portion. The medial portion is configured to be attached to sub-urethral or bladder neck tissues for providing a supporting force to the sub-urethral or bladder neck tissues, wherein arbitrary selectable discrete locations of the medial portion of the linear strip of mesh are defined to exhibit biomechanical characteristics in accordance with biomechanical characteristics at arbitrary selectable discrete locations of the sub-urethral or bladder neck tissues where the respective arbitrary selectable discrete locations of the medial portion are configured to be attached. The biomechanically compatible implant includes a first sleeve removably coupled to the proximal portion and configured be removed by pulling away a first elongate member that removably couples the first sleeve with the proximal portion. The biomechanically compatible implant further includes a first dilator configured to be attached to an end of the proximal portion of the linear strip of mesh.

The present invention provides a device to generate a biomechanically compatible implant pattern for an implant that behaves in accordance with biomechanical characteristics of a bodily tissue in an embodiment. The device includes a pressure unit for applying a defined pressure to a location on the bodily tissue. The device further includes a sensor for detecting a deformation caused by application of the defined pressure and a data analyzer to correlate values of the deformation and the defined pressure so as to determine a biomechanical characteristic pattern of the bodily tissue in response to the pressure. The device further includes a control unit to define an implant pattern based on the biomechanical characteristic pattern of the bodily tissue such that at an arbitrarily large plurality of discrete spatial coordinates, biomechanical characteristics of the implant conform with biomechanical characteristics at respective spatial locations of the bodily tissue where the respective spatial coordinates of the implant are configured to be positioned.

The present invention provides a system for developing a mesh-based implant in an embodiment. The system includes a modeling system for generating design models corresponding to the implant using a set of machine learning tools, modeling tools, and data sources acquired from a plurality of sources, wherein one of the data sources include subject's biomechanical characteristics at arbitrarily large number of locations of a bodily tissue where the implant is configured to be attached. The design models may be contained in a software file in an embodiment. The system further includes an additive manufacturing device configured to develop the implant by depositing layered structures, based on the design models contained in the software file that is readable and executable by the additive manufacturing device, so that, at arbitrarily large number of locations of a so fabricated implant, biomechanical characteristics conform with the biomechanical characteristics of the arbitrarily large number of locations of the bodily tissue where the arbitrarily large number of locations of the implant are configured to be attached.

BRIEF DESCRIPTION OF THE FIGURES

The invention and the following detailed description of certain embodiments thereof may be understood with reference to the following figures.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The terms "a" or "an," as used herein, are defined as one or more than one. The term "another," as used herein, is defined as at least a second or more. The terms "including" and/or "having", as used herein, are defined as comprising (i.e., open transition).

Figure 1:
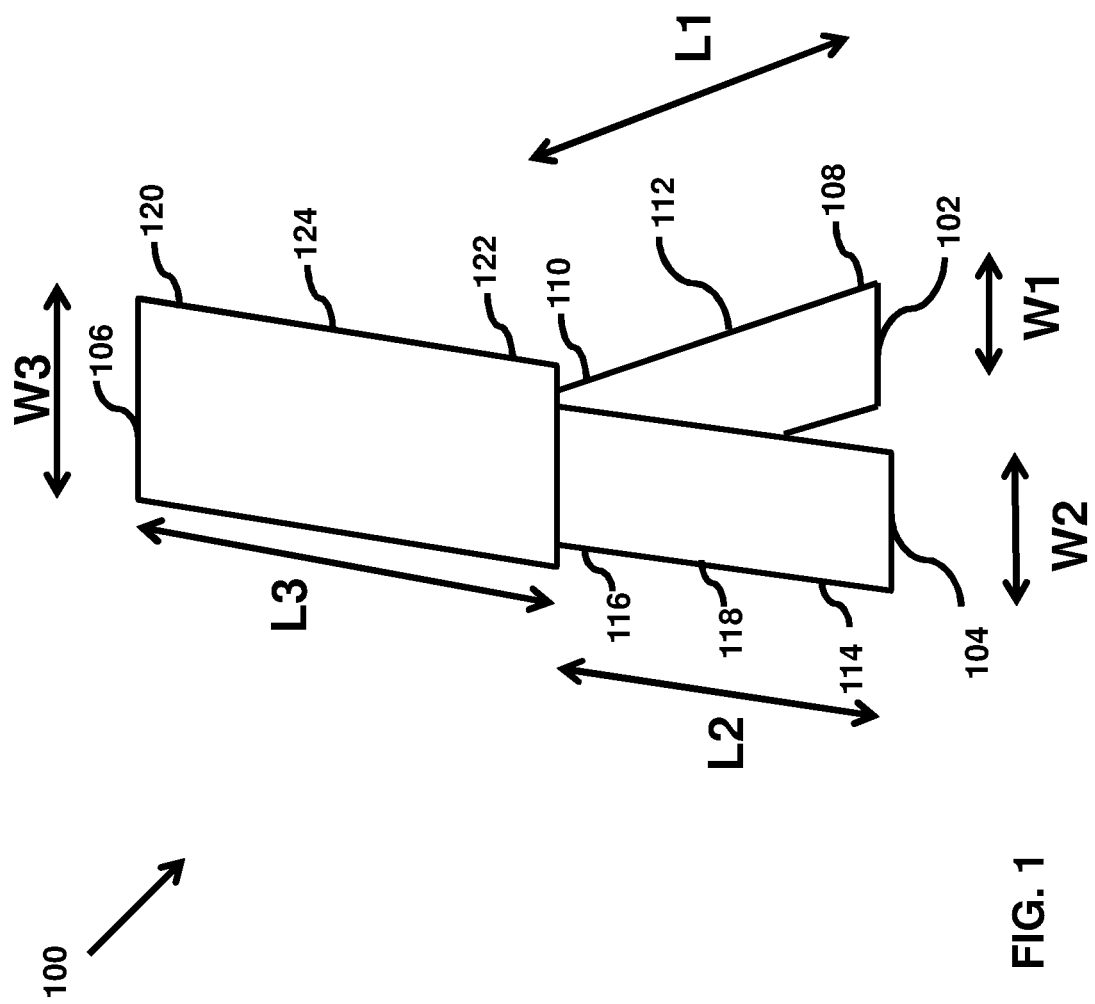
FIG. 1 illustrates a schematic diagram of an implant in accordance with an embodiment of the present invention.

FIG. 1 is a schematic diagram illustrating generally, among other things, an example of a system and an environment in which it can be used.

The embodiments of the present invention may be implemented in slings suitable for the treatment of male and female urinary and fecal incontinence and to effect pelvic floor, perineal floor, and pelvic prolapse repairs employing a variety of surgical approaches. For example, female pelvic floor repair slings such as urinary slings or pelvic prolapse repair slings may be implanted by techniques that involve transvaginal, transobturator, suprapubic, pre-pubic, or transperineal exposures or pathways, and male urinary incontinence slings may be implanted by techniques that involve transobturator, suprapubic, or transperineal pathways. The disclosed embodiments can be used as fecal incontinence slings which may be implanted by techniques that involve transvaginal, transobturator, suprapubic or via perineal floor pathways or through other methods or may be used for other uplift and reconstruction surgeries.

FIG. 1 illustrates a schematic diagram of an implant 100 in accordance with an embodiment of the present invention. The implant 100 includes a first flap 102, a second flap 104, and a third flap 106. The first flap 102 defines a first portion 108, a second portion 110, and a mid portion 112 such that a total length of the first flap is L1 and a total width of the first flap is W1. In another embodiment, the width of the first flap may vary across the length L1 gradually or in discrete portions. The second flap 104 defines a first portion 114, a second portion 116, and a mid portion 118 such that a total length of the second flap is L2 and a total width of the second flap is W2. In another embodiment, the width of the second flap 104 may vary across the length L2 gradually or in discrete portions. The third flap 106 defines a first portion 120, a second portion 122, and a mid portion 124 such that a total length of the third flap is L3 and a total width of the third flap is W3. In another embodiment, the width of the third flap 106 may vary across the length L3 gradually or in discrete portions. The three flaps 102, 104, and 106 can be defined rectangular or triangular or trapezoidal or curved in shape or may have any other shape. In an example, the three lengths L1, L2, and L3 may be equal or different. Similarly, the widths W1, W2, and, W3 may be equal or different.

In various embodiments, the implant 100 can be used for the treatment of a pelvic floor disorder. In some embodiments, the implant 100 can be used to suspend various bodily locations in a body of a patient such as pelvic organ of a patient's body such as for the treatment of pelvic organ prolapse. In some embodiments, the implant 100 can be used in a urinary sling with some modifications as will be discussed later. In some embodiments, the implant 100 can be used in a retropubic incontinence sling. In some embodiments, the implant 100 can be configured to be delivered by way of a transvaginal approach or a transobturator approach or vaginal pre-pubic approach or a laparoscopic approach or can be delivered through other methods and may be positioned at various locations within a patient's body without limitations. In some embodiments, the implant 100 can be delivered through a sacrocolpopexy procedure.

The first flap 102 may be configured to be attached to a first bodily portion. In an embodiment, the first bodily portion may be an anterior vaginal wall such that the first flap 102 may be configured to be positioned at the anterior vaginal wall. The second flap 104 may be configured to be attached to a second bodily portion. In an embodiment, the second bodily portion may be a posterior vaginal wall such that the second flap 104 may be configured to be positioned at the posterior vaginal wall. The third flap 106 may be configured to be attached to a third bodily portion. In an embodiment, the third bodily portion may be sacrum or tissues proximate the sacrum or lumbar vertebra, tail bone, or illium portion of hip bone or uterus, or any other location or nearby tissues such that the third flap 106 may be configured to be positioned at or proximate to the sacrum or lumbar vertebra, tail bone, and illium portion of hip bone or uterus or any other location or nearby tissues.

The first bodily portion may exhibit a definite biomechanical behavior in a defined set of physical conditions. For example, the first bodily portion may behave different than the second bodily portion. Even, two different locations at the first bodily portion may behave differently. For example two different locations at the anterior vaginal wall may behave differently. Similarly, two different locations at the second bodily portion may behave differently. For example, two different locations at the posterior vaginal wall may behave differently. In an example, five different locations at the anterior vaginal wall may behave differently and five different locations at the posterior vaginal wall may behave differently. In an example, arbitrary selectable different locations at the anterior vaginal wall may behave differently and arbitrary selectable different locations at the posterior vaginal wall may behave differently. In an example, arbitrary selectable large number of different locations at the anterior vaginal wall may behave differently and arbitrary selectable large number of different locations at the posterior vaginal wall may behave differently.

In an example, biomechanical behaviour of an anterior vaginal wall for a first patient may be different from biomechanical behaviour of an anterior vaginal wall of a second patient as same tissues or organs of different patients may behave differently and may exhibit varying biomechanical characteristics. This may be due to age, unique individual tissue characteristics, intra-abdominal force interactions or intra-abdominal pressures, pregnancy or childbirth for example pregnancy or childbirth may alter biomechanical characteristics of tissues of vaginal walls, obesity, body mass index (BMI), specific tissue characteristics, specific vaginal wall such as anterior vaginal wall or posterior vaginal wall may have different biomechanical characteristics, position or location of a tissue with respect to other tissues such as distance from abdomen or distance from uterus of a specific location of an anterior vaginal wall or a posterior vaginal wall, transmission of abdominal pressures to specific locations, anatomy of tissues at a specific location, orientation of tissues at a specific location with other tissues, composition of tissues at different locations such as collagen levels at different locations or in different tissues or of different persons, state and intensity of prolapse, types of prolapse, associated diseases to a subject, vaginal delivery, chronic increased intra-abdominal pressure caused by obesity, chronic respiratory disease and/or related cough, chronic constipation, repetitive occupational activities, heavy lifting, hormones, pelvic organ cancers and the like.

In an example, ligaments and the vaginal walls of young women may exhibit biomechanical behaviour different than those of older women. Furthermore, young women's tissues may differ slightly from older women's tissues. Aging and possibly diverse trauma may have an impact on the mechanical behaviour of pelvic floor tissues. Over time pelvic floor ligaments and vaginal tissues may differentiate and acquire different mechanical behaviour. In an example, biomechanical characteristics of vaginal tissues or vaginal walls between women with and without pelvic organ prolapse (POP) may vary. In an example, the occurrence of POP may raise values of stiffness (E) and maximum stress in the anterior vaginal wall. Women with severe anterior vaginal prolapse may present higher levels of stiffness and maximum stress compared to those with lower POP stages. In an example, women with POP may present significant changes of biomechanical properties in the vagina. In an example, virgin tissues may be more elastic and strong. Pregnancy may have a great impact on tissue composition and biomechanical properties. Biochemical changes in tissue protein composition may in an example cause altered biomechanical properties. In an example, vaginal tissues may show significantly higher total collagen and glycosaminoglycan values nearest the cervix. In an example, a proximal region of vaginal wall may be the stiffest (Young's modulus, $p<0.05$), strongest (maximum stress, $p<0.05$) compared to distal region, and may be the most elastic (such as permanent strain) according to one study. In an example, the form, size, and situation of the uterus may vary at different periods of lifetime and under different circumstances which may cause changes in interactions of the forces and alter biomechanical characteristics at other tissues or organs at the same time changing biomechanical characteristics of uterus itself. In an example, more obese women may have stiffer tissue properties.

In an example, the first flap 102 (that may be configured to be attached to the anterior vaginal wall) may be defined such that at least two different locations of the first flap 102 exhibit biomechanical characteristics in accordance with the biomechanical characteristics of at least two different locations of the anterior vaginal wall where the respective two different locations of the first flap 102 are configured to be attached. In an example, the first flap 102 may be defined such that at least five different locations of the first flap 102 exhibit biomechanical characteristics in accordance with the biomechanical characteristics of five different locations of the anterior vaginal wall where the respective five different locations of the first flap 102 are configured to be attached. In another example, the first flap 102 may be defined such that arbitrary selectable different locations of the first flap 102 exhibit biomechanical characteristics in accordance with the biomechanical characteristics at the arbitrary selectable different locations of the anterior vaginal wall where the respective arbitrary selectable different locations of the first flap 102 are configured to be attached. In an example, the first flap 102 may be defined such that arbitrary selectable large number of different locations of the first flap 102 exhibit biomechanical characteristics in accordance with the biomechanical characteristics at the arbitrary selectable large number of different locations of the anterior vaginal wall where the respective arbitrary selectable large number of different locations of the first flap 102 are configured to be attached. In this way, the first flap 102 may be configured to define the biomechanical characteristics at different locations so as to emulate the biomechanical behavior of the first bodily portion such as the anterior vaginal wall at different arbitrary selectable locations. The biomechanical characteristics of the first flap 102 and the first bodily portion can be identified through a set of numerical values that may signify a degree or measure of the biomechanical characteristics of a particular type. For example, the biomechanical characteristics can represent elasticity and a corresponding numerical value can define modulus of elasticity or a degree of elasticity of the first flap at a particular location or of the anterior vaginal wall at a particular location. In some embodiments, the biomechanical characteristics can represent stiffness. In some embodiments, the biomechanical characteristics can represent strength. In some embodiments, the biomechanical characteristics can represent resistance to creep. In some embodiments, the biomechanical characteristics can represent hyperelasticity. In some embodiments, the biomechanical characteristics can represent viscohyperelasticity. In some embodiments, the biomechanical characteristics can represent anisotrophicity. In some embodiments, the biomechanical characteristics can represent maximum stress, hysteresis, extensibility (the capacity to be stretched), plasticity (the property to get permanently changed by a deforming force), and torsion (the capacity to be deformed when exposed to a torsional force), stiffness index, stretch ratio, and the like. In various embodiments, the first flap 102 may be configured so that one or more of elasticity, hyperelasticity, resistance to creep, stiffness, strength, maximum stress, hysteresis, extensibility, plasticity, and torsion, stiffness index, stretch ratio, and other such characteristics (without limitations) of the first flap 102 is in accordance with elasticity, hyperelasticity, resistance to creep, stiffness, strength, maximum stress, hysteresis, extensibility (the capacity of skin to be stretched), plasticity (the property of skin when it is permanently changed by a deforming force), and torsion (the capacity of skin to be deformed when exposed to a torsional force), stiffness index, stretch ratio, and the like properties of the anterior vaginal wall at the arbitrary selectable different locations.

In an example, the second flap 104 (that may be configured to be attached to the posterior vaginal wall) may be defined such that at least two different locations of the second flap 104 exhibit biomechanical characteristics in accordance with the biomechanical characteristics of at least two different locations of the posterior vaginal wall where the respective two different locations of the second flap 104 are configured to be attached. In an example, the second flap 104 may be defined such that at least five different locations of the second flap 104 exhibit biomechanical characteristics in accordance with the biomechanical characteristics of five different locations of the posterior vaginal wall where the respective five different locations of the second flap 104 are configured to be attached. In an example, the second flap 104 may be defined such that arbitrary selectable different locations of the second flap 104 exhibits biomechanical characteristics in accordance with the biomechanical characteristics at the arbitrary selectable different locations of the posterior vaginal wall where the respective arbitrary selectable different locations of the second flap 104 are configured to be attached. In an example, the second flap 104 may be defined such that arbitrary selectable large number of different locations of the second flap 104 exhibits biomechanical characteristics in accordance with the biomechanical characteristics at the arbitrary selectable large number of different locations of the posterior vaginal wall where the respective arbitrary selectable large number of different locations of the second flap 104 are configured to be attached. In this way, the second flap 104 may be configured to define the biomechanical characteristics at different locations so as to emulate the biomechanical behaviour of the second bodily portion such as the posterior vaginal wall at different locations. The biomechanical characteristics of the second flap 104 and the second bodily portion can be identified through a set of numerical values that may signify a degree or measure of the biomechanical characteristics of a particular type such as those discussed above with respect to the first flap 102.

In an example, the third flap 106 (that may be configured to be attached to the third bodily portion) may be defined such that at least two different locations of the third flap 106 exhibit biomechanical characteristics in accordance with the biomechanical characteristics of at least two different locations of the third bodily portion where the respective at least two different locations of the third flap 106 are configured to be attached. In an example, the third flap 106 may be defined such that five different locations of the third flap 106 exhibits biomechanical characteristics in accordance with the biomechanical characteristics of five different locations of the third bodily portion where the respective five different locations of the third flap 106 are configured to be attached. In an example, the third flap 106 may be defined such that arbitrary selectable different locations of the third flap exhibit biomechanical characteristics in accordance with the biomechanical characteristics at the arbitrary selectable different locations of the third bodily portion where the respective arbitrary selectable different locations of the third flap 106 are configured to be attached. In an example, the third flap 106 may be defined such that arbitrary selectable large number of different locations of the third flap 106 exhibit biomechanical characteristics in accordance with the biomechanical characteristics at the arbitrary selectable large number of different locations of the third bodily portion where the respective arbitrary selectable large number of different locations of the third flap 106 are configured to be attached. In this way, the third flap 106 may be configured to define the biomechanical characteristics at different locations so as to emulate the biomechanical behaviour of the third bodily portion. The biomechanical characteristics of the third flap 106 and the third bodily portion can be identified through a set of numerical values that may signify a degree or measure of the biomechanical characteristics of a particular type such as those discussed above.

In various embodiments, the biomechanical characteristics of the first flap 102 or the second flap 104 or the third flap 106 can be defined or varied for example by defining or varying one or more of shape, size, fabrication method, structure, profile, knit structure, pore size, material of fabrication, fiber orientation, knit pattern, weave pattern, pore construct, knit structure, knitting pattern, weaving pattern, mesh strands, fibres with holes or without holes, number of such holes in fibres per unit length or number of cells per unit length longitudinally or in a transverse direction or in any other direction and the like. In some embodiments, for example, the biomechanical characteristics of the first flap 102 or the second flap 104 or the third flap 106 can be varied by varying shape. For example, the first flap 102 which may be configured to be attached to the anterior vaginal wall may be defined by pores with a square, rectangular, triangular or any other shape or a combination of these shapes, at different locations of the first flap 102 so as the first flap 102 to closely behave in accordance with the biomechanical behaviour of the anterior vaginal wall at different locations. In some embodiments, a specific type of material may be used to fabricate a particular portion of the first flap 102 or the second flap 104 or the third flap 106 so as to provide a desired biomechanical characteristic. For example, a viscoelastic medical grade polymer with necessary viscoelasticity can be used for fabricating a specific portion to provide a desired viscoelastic characteristic. In embodiments, several different portions (such as 2, 3, 4, 5, 6, 7, 8, 9, 10 or even more arbitrary selectable locations) of the first flap 102 may be provided with different shape, size, fabrication method, structure, profile, knit structure, pore size, material of fabrication, fibre orientation, knit pattern, weave pattern, pore construct, knit structure, knitting pattern, weaving pattern, mesh strands, fibres with holes or without holes, number of such holes in fibres per unit length or number of cells per unit length longitudinally or in a transverse direction or in any other direction or a combination of these, and the like. Similarly, in embodiments, several different portions (such as 2, 3, 4, 5, 6, 7, 8, 9, 10 or even more or arbitrary selectable portions) of the second flap 104 may be provided with different shape, size, fabrication method, structure, profile, knit structure, pore size, material of fabrication, fibre orientation, knit pattern, weave pattern, pore construct, knit structure, knitting pattern, weaving pattern, or a combination of these, and the like. Therefore, the same flap such as the first flap 102 or the second flap 104 or the third flap 106 may include even more than one type of pore constructs, shape, size, fabrication method, structure, profile, knit structure, pore size, material of fabrication, fibre orientation, knit pattern, weave pattern, pore construct, knit structure, knitting pattern, weaving pattern, mesh strands, fibres with holes or without holes, number of such holes in fibres per unit length or number of cells per unit length longitudinally or in a transverse direction or in any other direction or may even include a combination of these ways without limitations for achieving desired biomechanical characteristics. In an example, in case of a mesh-based implant, several different portions of the same flap may be woven or knit with different tensioning force so as to achieve a desired biomechanical characteristic at a particular location of the first flap 102 or the second flap 104 or the third flap 106. In accordance with various embodiments, various other ways of obtaining desired biomechanical characteristics may be employed without limitations. In accordance with embodiments, a particular way of providing desired biomechanical characteristics may be used either alone or in combination with other ways. The implant 100 may be a mesh-based structure or a planar structure without any mesh structure. Accordingly, select ways of achieving a desired biomechanical characteristic may be used based on whether the mesh-based implant is used or the non-mesh based implant is used.

The anterior vaginal wall and the posterior vaginal wall may exhibit different biomechanical properties along different directions even at the same location due to anisotropic nature. In some embodiments, the first flap 102 and the second flap 104 may therefore be configured to behave differently along different directions such as in a longitudinal direction or in a transverse direction or in any other direction. Various ways of maintaining and achieving desired biomechanical characteristics as discussed above may be employed and combined in a manner so as to get a desired biomechanically compatible implant that behaves in accordance with the behaviour of the anterior vaginal wall and the posterior vaginal wall at different locations and in different directions.

Figure 2:
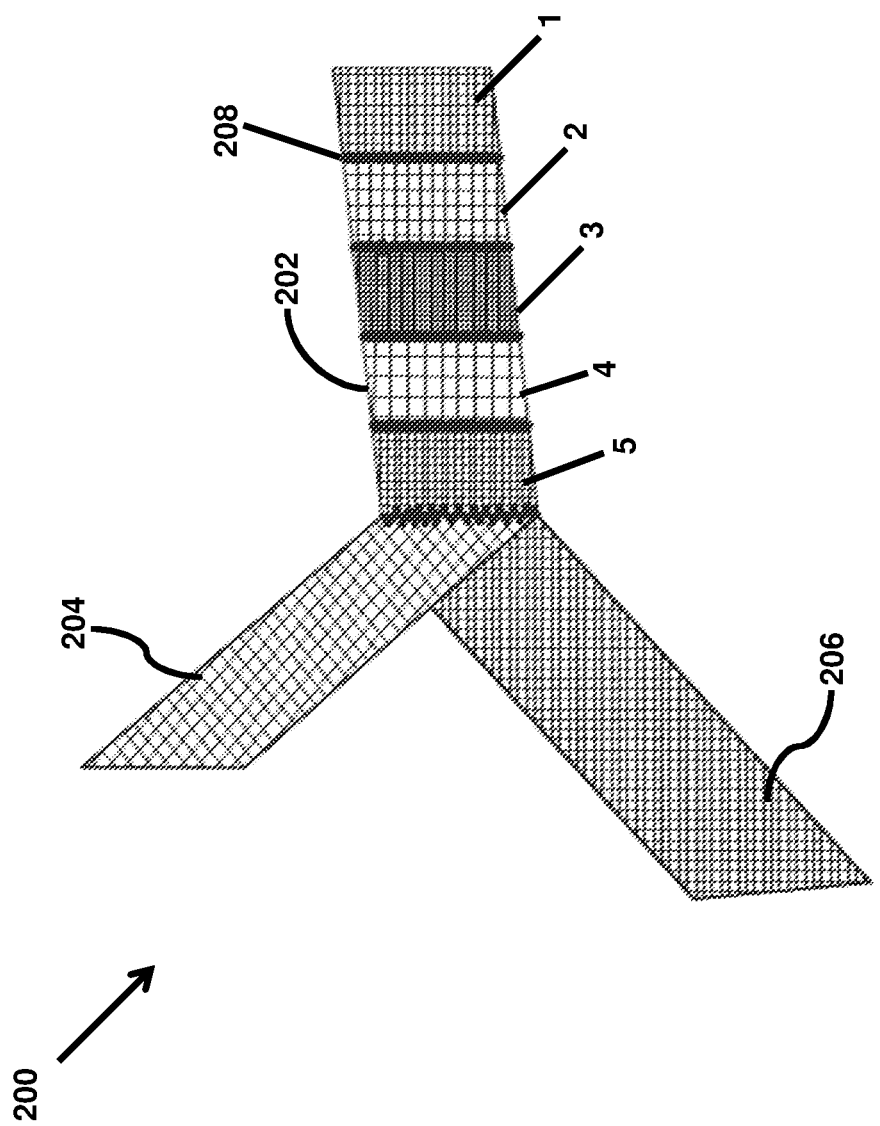
FIGS. 2-9 illustrate schematic diagrams of an implant for prolapse repair in accordance with different embodiments of the present invention.

In an embodiment, the implant 100 can be configured as a Y-shaped mesh-based implant 200 as shown in FIG. 2. FIG. 2 illustrates a schematic view of the mesh-based implant 200 (interchangeably referred to as implant 200 merely for simplicity of description) in accordance with an embodiment of the present invention. As shown, the implant 200 includes a first flap 202 similar to the first flap 102, a second flap 204 similar to the second flap 104, and a third flap 206 similar to the third flap 106. In accordance with the illustrated embodiments of FIG. 2, the first flap 202, the second flap 204 and the third flap 206 are made of a mesh structure. The mesh structure can be fabricated from a natural material or a synthetic material.

In some embodiments, the implant 200 is made of a synthetic material such as a polymeric material and the like. In some embodiments, the implant 200 includes a polymeric mesh body. The mesh body may comprise a chain link fence-like design. In such designs, the fibers or strands of the mesh may be woven, linked, or otherwise connected, and may share the stress of a supported load. In other embodiments, the implant 200 may include a polymeric planar body without mesh cells and structures. Exemplary polymeric materials are polypropylene, polyester, polyethylene, nylon, PVC, polystyrene, and the like. In some embodiments, the implant 200 is made of a non-woven polymeric material. In some other embodiments, the implant 200 can be made of natural materials such as biologic material or a cadaveric tissue and the like. Additionally, in some embodiments, the implant 200 is stretchable and flexible to adapt movements along the anatomy of the human body. In some embodiments, the attributes such as softness, lightness, conformity and strength may be required in the implant 200 for efficient tissue repair and implantation. In some embodiments, the implant 200 can be made of biodegradable materials. In some embodiments, the implant 200 can be made of non-biodegradable material. In some embodiments, the implant 200 can be made of medical grade materials.

In an example, the first flap 202, the second flap 204, and the third flap 206 can be configured to be attached to the first bodily portion, the second bodily portion, and the third bodily portion as discussed in conjunction with FIG. 1. In the illustrated mesh-based implant 200, the first flap 202 is defined by first biomechanical characteristics at location (or region or portion or location referred interchangeably throughout the document) 1, second biomechanical characteristics at location 2, third biomechanical characteristics at location 3, fourth biomechanical characteristics at location 4, and fifth biomechanical characteristics at location 5 such that the five different locations of the first flap 202 will behave differently when attached to the anterior wall where the first flap 202 is configured to be attached to. The different biomechanical behaviour of the first flap 202 at five different locations is in accordance with different biomechanical behaviour of the anterior vaginal wall at five different locations where the five different locations of the first flap 202 are configured to be attached to. In an embodiment, a location at a bodily portion or a flap as discussed in the document may represent specific spatial coordinate or a region bounded within a plurality of spatial coordinates. In an embodiment, a location of the mesh-based flap such as 202 may represent one pore such that different locations reflect different regions covered by different pores of the flap 202. As shown in FIG. 2, the different biomechanical characteristics at the five depicted locations 1, 2, 3, 4, and 5 are obtained by varying pore sizes in the five depicted locations, in an embodiment. It must be appreciated, that the varying biomechanical characteristics can be defined based on requirements using other ways or a combination of ways such as those discussed earlier in conjunction with FIG. 1.

Figure 3:
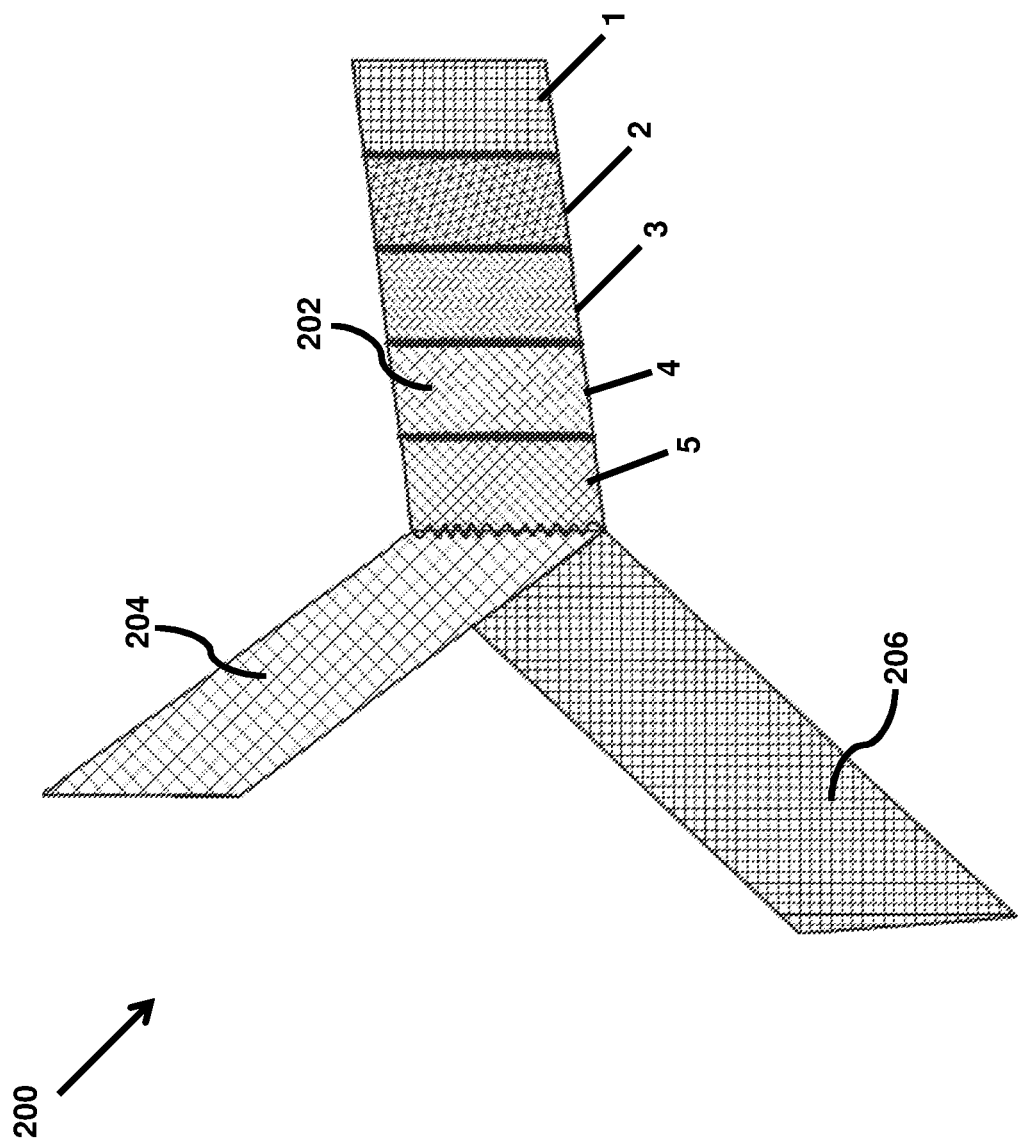

In accordance with an embodiment, FIG. 3 illustrates the implant 200 with the five different locations location 1, location 2, location 3, location 4, and location 5 (referred interchangeably as five different locations or five locations or five regions or five portions) having varying biomechanical characteristics obtained by a combination of varying pore sizes, pore shapes, and orientations of fibres. The pore sizes in any two or more of the locations may be equal or different in various embodiments in order to define the required biomechanical characteristics. In an embodiment, the first flap 202 may include a shift region such as a shift region 208 between two portions with different biomechanical characteristics. The shift region 208 may be mesh-based or non-mesh based such as a planar structure. The shift region 208 may include a different type of knit pattern in an embodiment. In an example, the shift region such as 208 may merely include a few sutures or fibres that may join the different locations such as location 1 and location 2. In an example, there may not be any shift region similar to 208 and the different regions with different biomechanical properties may simply couple directly with one another.

Figure 4:
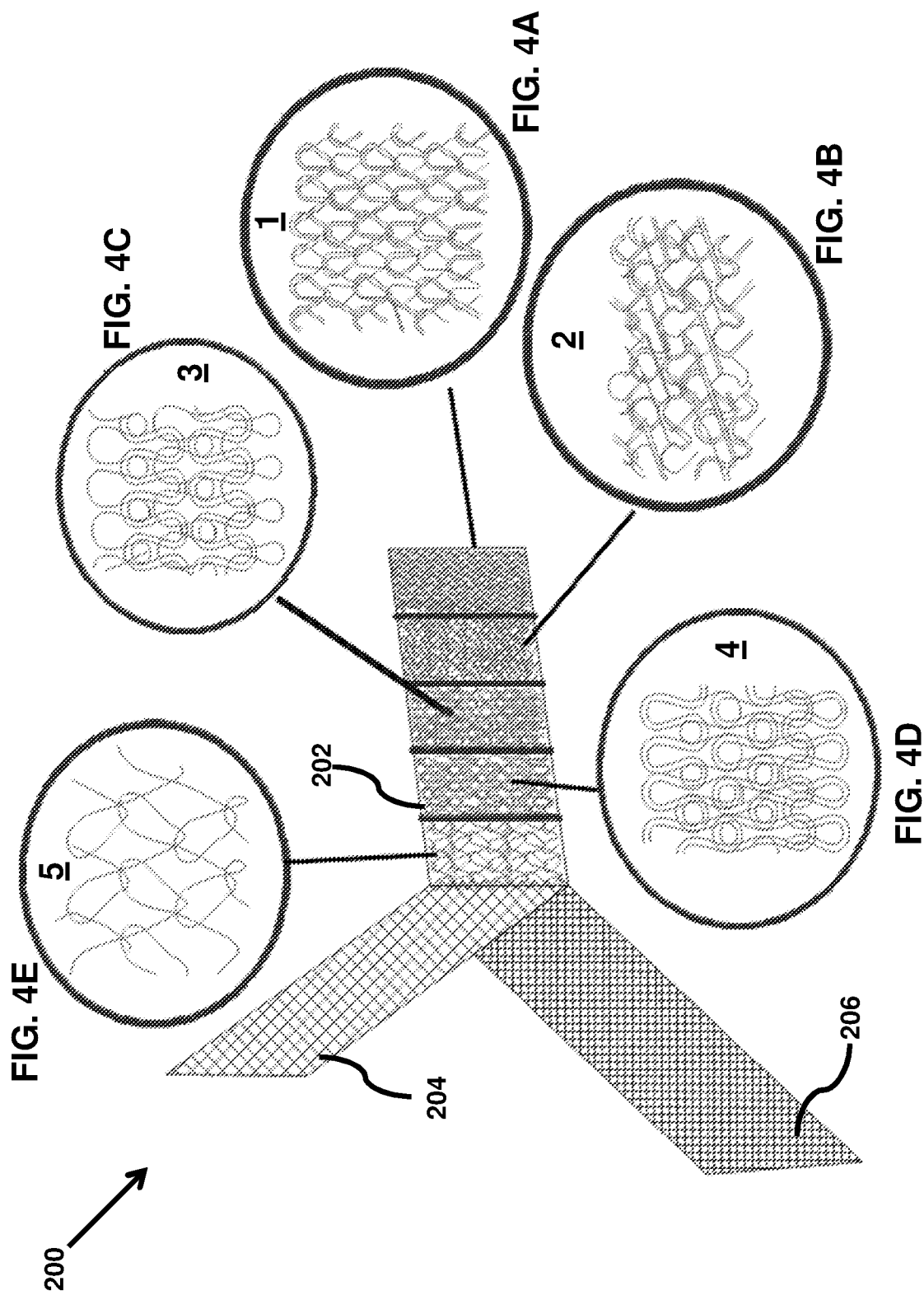

In accordance with an embodiment, FIG. 4 illustrates another embodiment of the implant 200 with five different types of knit structures at the five different locations 1, 2, 3, 4, and 5 (1-5) of the first flap 202 so as to define different types of biomechanical characteristics at the five different locations 1-5 of the first flap 202. As depicted in FIGS. 4A, 4B, 4C, 4D, and 4E, the five different knit patterns can be obtained by knitting material fibres in different ways with specifically controlled knit parameters such as to result in defined biomechanical characteristics in the different locations 1-5.

Figure 5:
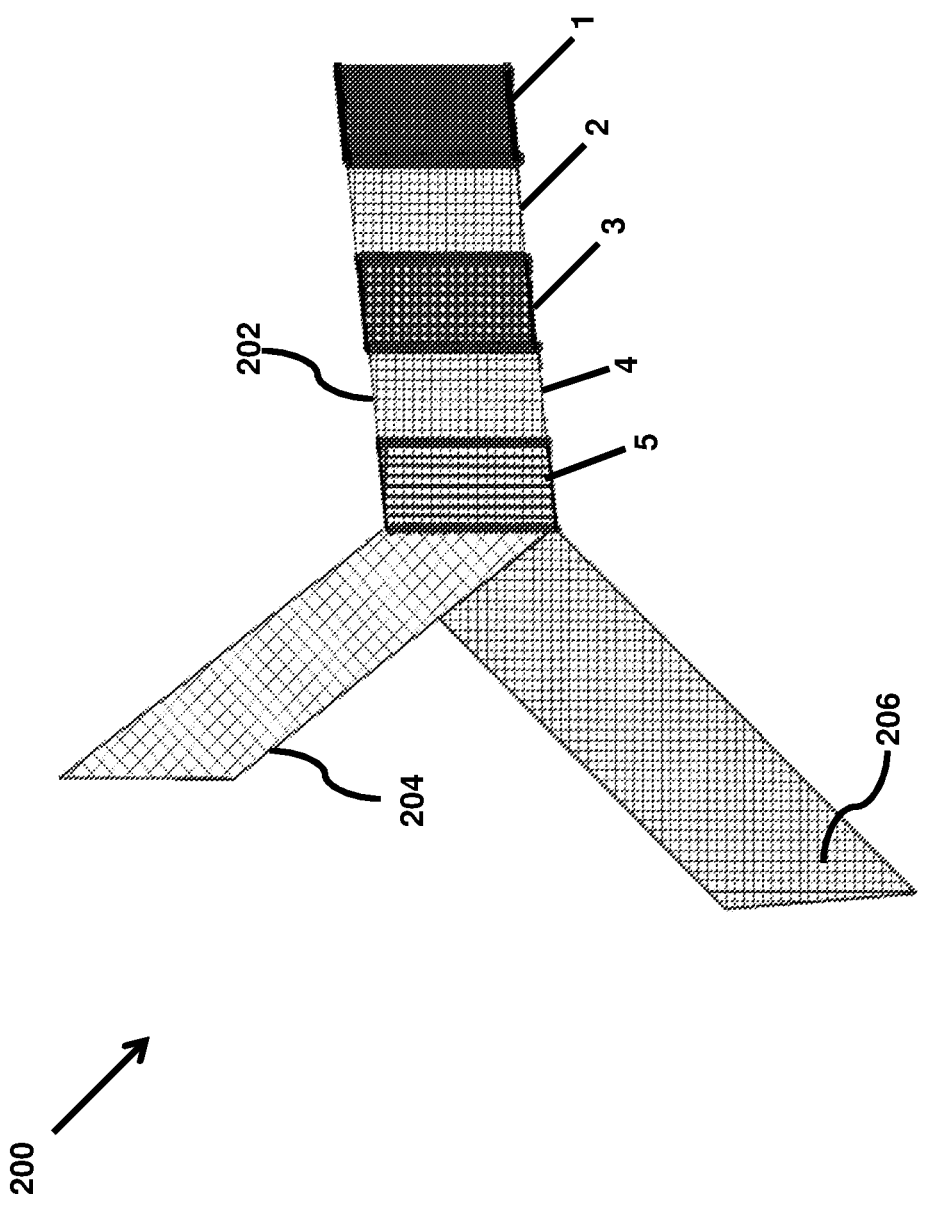
Figure 6:
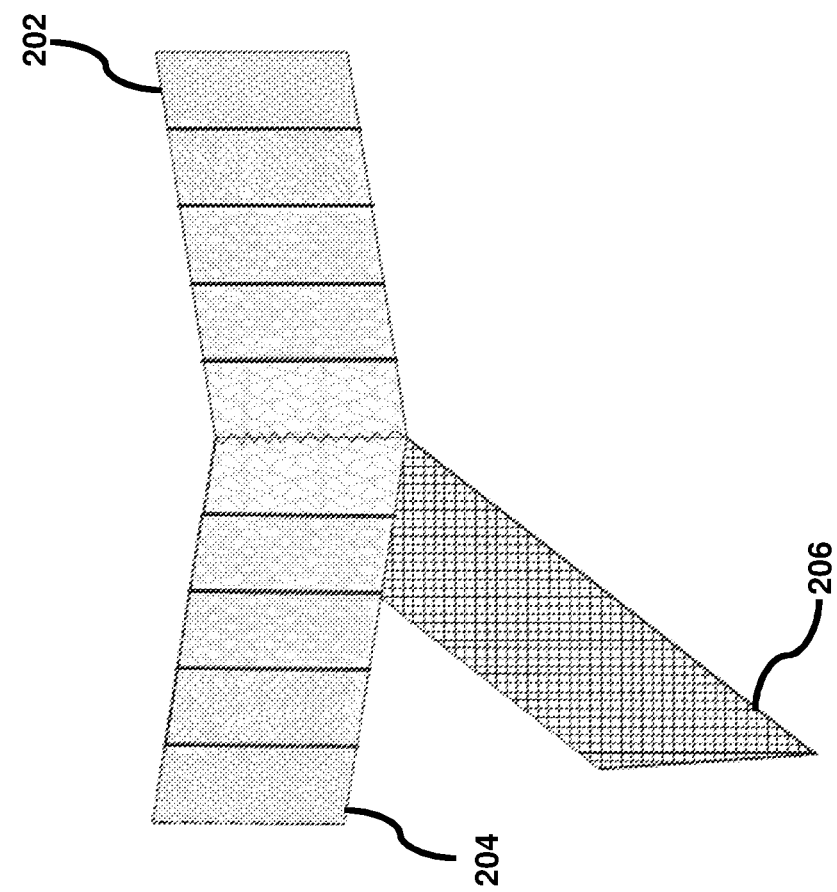
Figure 7:
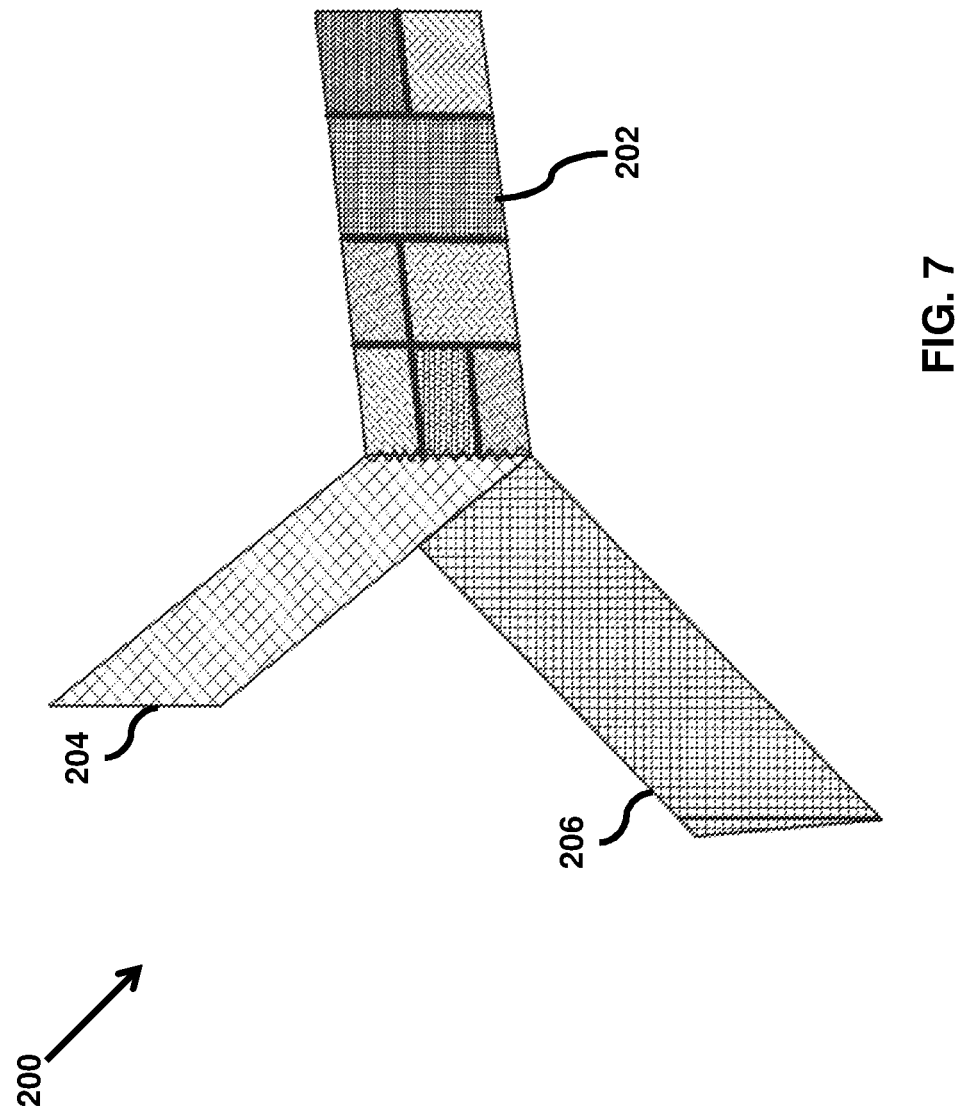
Figure 8:
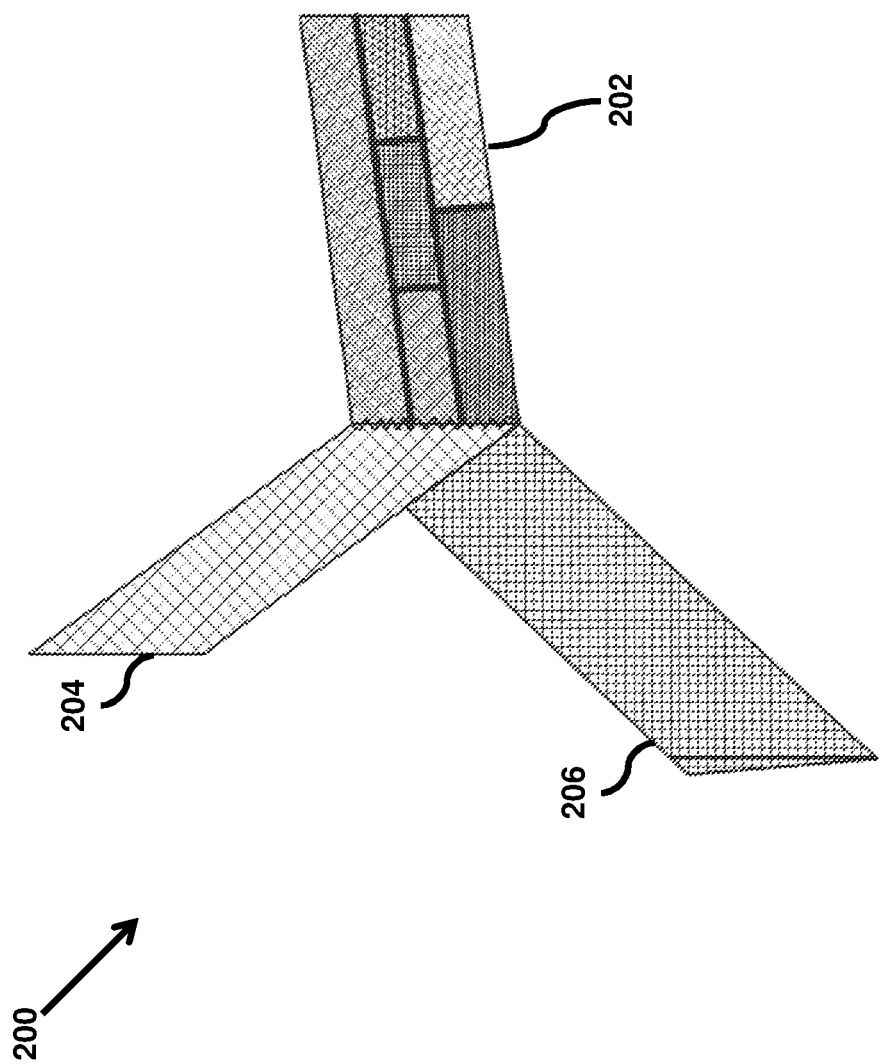

FIG. 5 illustrates another example of the implant 200 with five different types of coatings applied to the five different locations of the first flap 202 or made of five different materials having different biomechanical properties for example. In a similar manner, the first flap 202 can be defined and configured to behave in accordance with behaviour of the anterior vaginal wall using other ways or a combination of those ways. In an example, area covered by each location of the first flap can be reduced so as to customize and vary the biomechanical characteristics across smaller regions thereby more accurately emulating behaviour of the anterior vaginal wall. For example, using computerized and intelligent modeling and fabrication techniques as discussed later, the area of each region or location or portion can be reduced to pore levels or reduced even further or to micro levels such that the first flap 202 may be distributed to hundreds of locations or portions or regions or arbitrary selectable locations or portions or regions with each location or region having different biomechanical characteristics than the other at least to some extent in one or the other way of characteristics and in one or the other direction. The FIGS. 2-5 illustrate configuration of the first flap 202 as an example. Similarly, the second flap 204 can be configured for variations in the biomechanical properties across different regions or locations so as the second flap 204 to behave in accordance with the posterior vaginal wall such as shown in FIG. 6 with both the first flap 202 and the second flap 204 with varying knit structures across five different regions. Similarly, the third flap 206 can be configured for variations in the biomechanical properties across different regions or locations so as the third flap 206 to behave in accordance with the third bodily portion. In some embodiments, the third flap 206 may not include different configurations at different locations and the entire third flap 206 may be fabricated and defined to include a single pattern or material or structure etc. In an example, a location of the first flap 202 or the second flap 204 or the third flap 206 with defined and same biomechanical characteristics can extend over an entire length or width of the first flap 202 or the second flap 204 or the third flap 206. In an example, a location of the first flap 202 or the second flap 204 or the third flap 206 with defined and same biomechanical characteristics (also referred to as locations or regions of same biomechanical characteristics) may not extend over an entire width or length of the first flap 202 or the second flap 204 or the third flap 206 as shown in FIG. 7 with respect to the first flap 202 where one or more of the locations of same biomechanical characteristics of the first flap 202 may extend over a portion of the width. In a similar manner, the locations may or may not extend over a portion of the length such as shown in FIG. 8.

Figure 9:
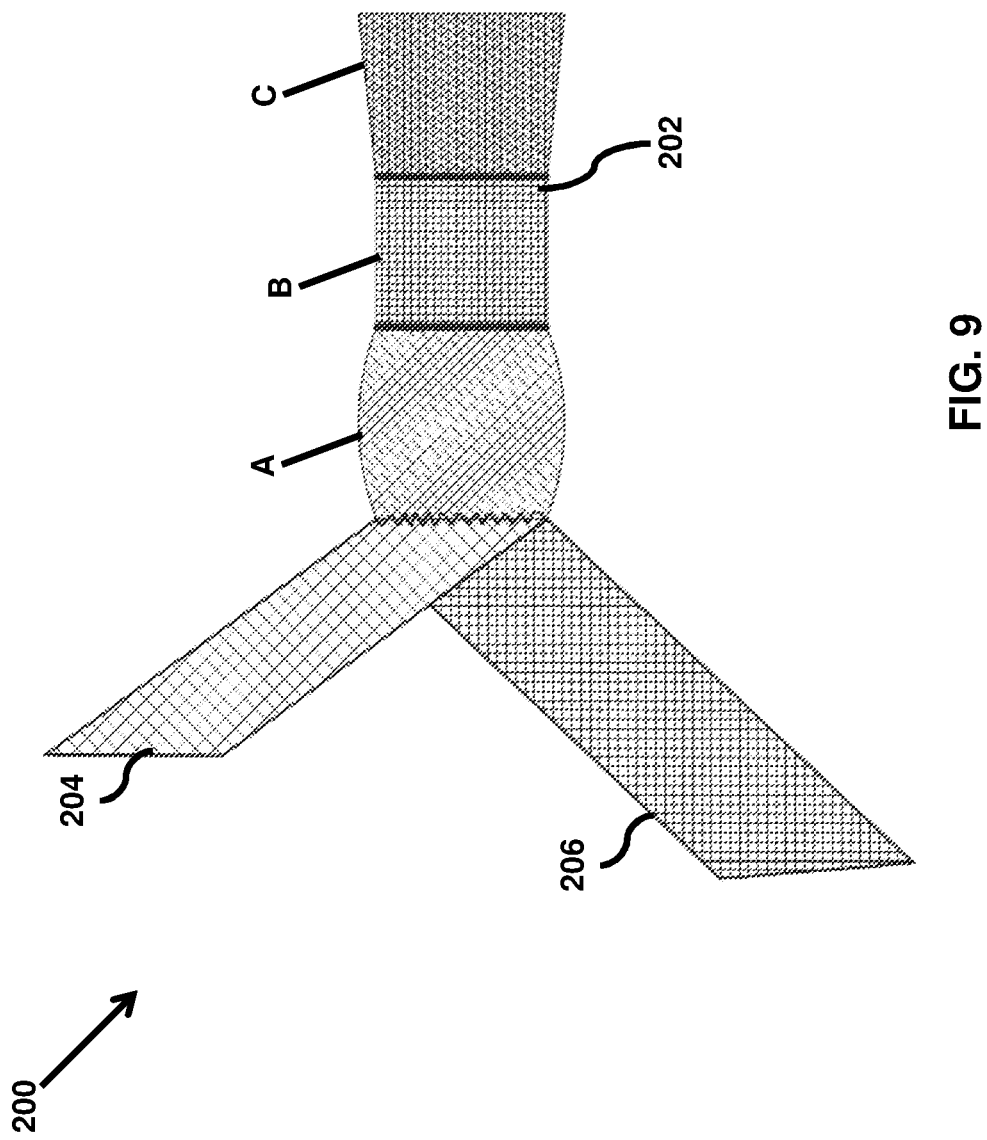

In accordance with an embodiment, the implant 200 may be configured for different shapes at different arbitrary locations. As shown in FIG. 9, the shapes of the implant 200 at three different locations A, B, and C or regions vary such that at a first location A, the shape is curved, at a second locations B, the shape is rectangular, and at a third location C, the shape is trapezoidal. Similarly, the shapes can be varied at arbitrary selectable different locations in embodiments. The varying shapes may be defined based on anatomical structure at a particular location of bodily tissues and based on biomechanical characteristics desired at a particular location.

The various embodiments discussed above in conjunction with FIGS. 1-9 with respect to the first flap 202 or the second flap 204 may be defined with respect to the first flap 202 or the second flap 204 or the third flap 206 without limitations in various embodiments.

The implant 100 or 200 illustrated in conjunction with FIGS. 1-9 may be configured such that one or two flaps of the three flaps 202, 204, and 206 of the Y-shape implant 100 or 200 can be fabricated as a conventional mesh or non-mesh strip such that the biomechanical characteristics of the one or two flaps may not vary substantially at different arbitrary selectable locations or regions or at two or more than two locations or regions of the respective one or two flaps. In an embodiment, the Y-shaped implant 200 can be fabricated as a single piece with the three flaps 202 or 204 or 206 such that the three flaps 202 or 204 or 206 extend from one another. In another embodiment, the three flaps 202 or 204 or 206 of the implant 200 may be fabricated separately and then can be coupled together before placement such as by a physician or a surgeon etc. In other embodiments, the implant 200 can be configured to define another shape such as a rectangular, square, trapezoidal, curved, or any other shape.

Figure 10:
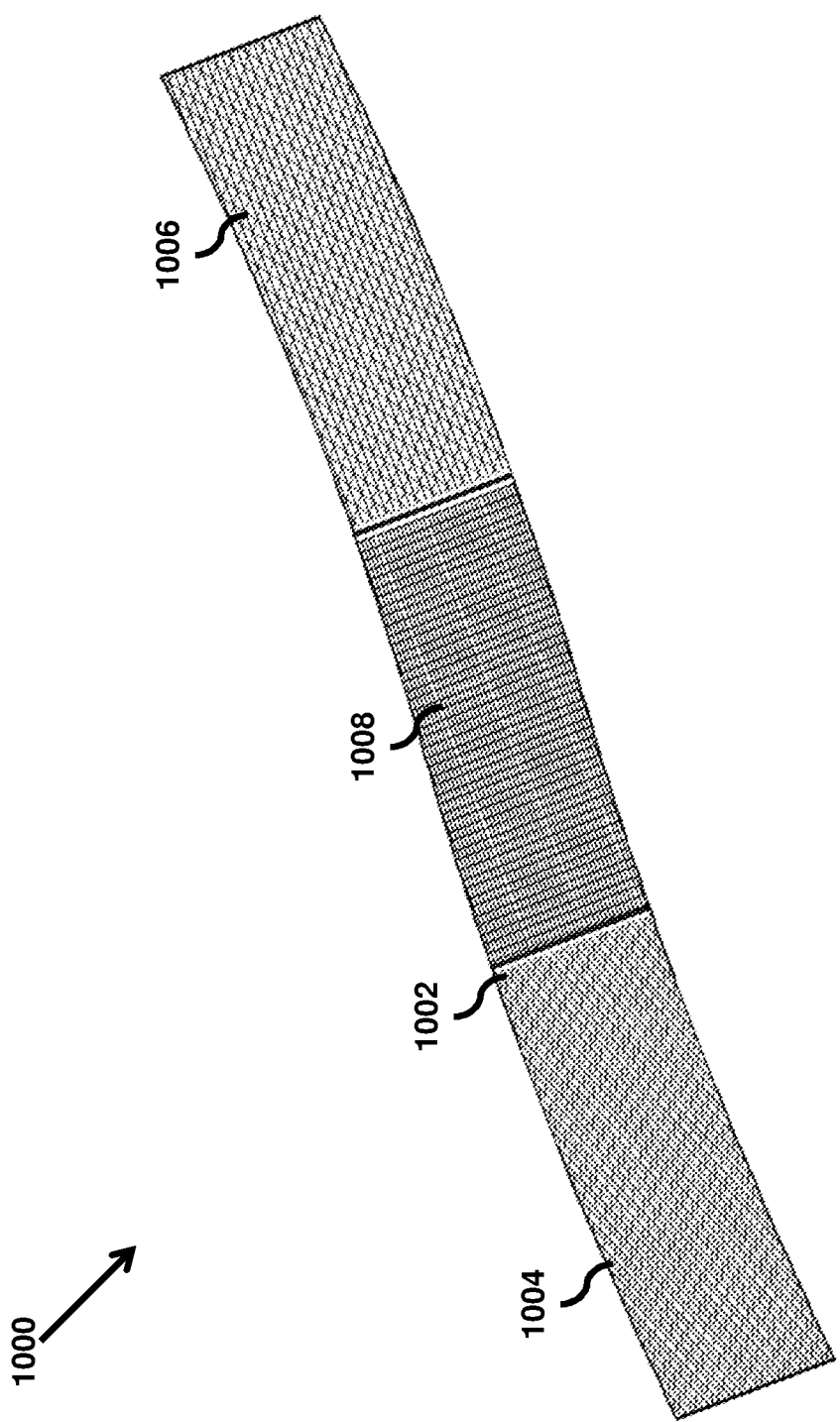
FIG. 10 illustrates an implant for repair of urinary incontinence in an embodiment of the present invention.

FIG. 10 illustrates an example of an implant 1000 defined as a linear strip of mesh and configured to support urethra or bladder neck or proximate tissues for preventing leakage of urine due to incontinence. The implant 1000 may include an elongate body member 1002 with a first portion 1004, a second portion 1006, and a medial portion 1008.

The first portion 1004 may be configured to be attached to a first bodily portion. The second portion 1006 may be configured to be attached to a second bodily portion. The medial portion 1008 may be configured to be attached to a third bodily portion. In an embodiment, the third bodily portion may be suburethral tissues, urethra, bladder neck, or nearby tissues such that the medial portion 1008 may be configured to be positioned at or proximate to the suburethral tissues, urethra, bladder neck, or nearby tissues or any other location or nearby tissues thereof.

The third bodily portion may exhibit a definite biomechanical behaviour in a defined set of physical conditions. For example, the third bodily portion may behave differently than the second bodily portion and the first bodily portion. Even, two different locations at the third bodily portion may behave differently. For example two different locations or regions at tissues underneath the urethra or bladder neck may behave differently. Similarly, two different locations at the second bodily portion or the first bodily portion may behave differently. In an example, five different locations at the third bodily portion may behave differently. In an example, arbitrary selectable different locations at the third bodily portion may behave differently. In an example, arbitrary selectable large number of different locations at the third bodily portion may behave differently.

In an example, biomechanical behaviour of the third bodily portion for a first patient may be different from biomechanical behaviour of the third bodily portion of a second patient as same tissues or organs of different patients may behave differently and may exhibit varying biomechanical characteristics. This may be due to age, unique individual tissue characteristics, intra-abdominal force interactions or intra-abdominal pressures or other factors mentioned elsewhere in the document.

In an example, the medial portion 1008 may be defined such that at least two different locations of the medial portion 1008 exhibit biomechanical characteristics in accordance with biomechanical characteristics of at least two different locations of the third bodily portion where the respective two different locations of the medial portion 1008 are configured to be attached. In an example, the medial portion 1008 may be defined such that at least five different locations of the medial portion 1008 exhibit biomechanical characteristics in accordance with the biomechanical characteristics of five different locations of the third bodily portion where the respective five different locations of the medial portion 1008 are configured to be attached. In an example, the medial portion 1008 may be defined such that arbitrary selectable different locations of the medial portion 1008 exhibit biomechanical characteristics in accordance with biomechanical characteristics of arbitrary selectable different locations of the third bodily portion where the respective arbitrary selectable different locations of the medial portion 1008 are configured to be attached. In an example, the medial portion 1008 may be defined such that arbitrary selectable large number of different locations of the medial portion 1008 exhibit biomechanical characteristics in accordance with biomechanical characteristics of arbitrary selectable large number of different locations of the third bodily portion where the respective arbitrary selectable different locations of the medial portion 1008 are configured to be attached. In this way, the medial portion 1008 may be configured to define the biomechanical characteristics at different locations so as to emulate the biomechanical behaviour of the third bodily portion such as sub urethral tissues or urethra or bladder neck or other proximate tissues at different locations. The biomechanical characteristics of the medial portion 1008 can be identified through a set of numerical values as discussed earlier above in conjunction with various figures. The various biomechanical characteristics discussed above in conjunction with other embodiments can be considered for the implant 1000. In a similar manner, optionally, the first portion 1004 and the second portion 1006 may also be configured to behave in accordance with the first bodily portion and the second bodily portion respectively.

In various embodiments, the large number of arbitrary selectable different locations may be defined and biomechanical characteristics thereon may be determined using computer-based and automated systems such that the large number may be hundreds of locations or even more such that the computer-based or automated system may create a pattern or biomechanical characteristics gradient across a bodily tissue or a portion of the bodily tissue.

In various embodiments, the biomechanical characteristics of the first portion 1004, the second portion 1006, and the medial portion 1008 can be defined or varied for example by defining or varying one or more of shape, size, fabrication method, structure, profile, knit structure, pore size, material of fabrication, fibre orientation, knit pattern, weave pattern, pore construct, knit structure, mesh strands/fibres with holes or without holes or number of such holes in fibres per unit length or number of cells per unit length longitudinally or in a transverse direction or in any other direction or may even include a combination of these ways for obtaining desired biomechanical characteristics and the like as discussed above in conjunction with other embodiments.

Figure 11:
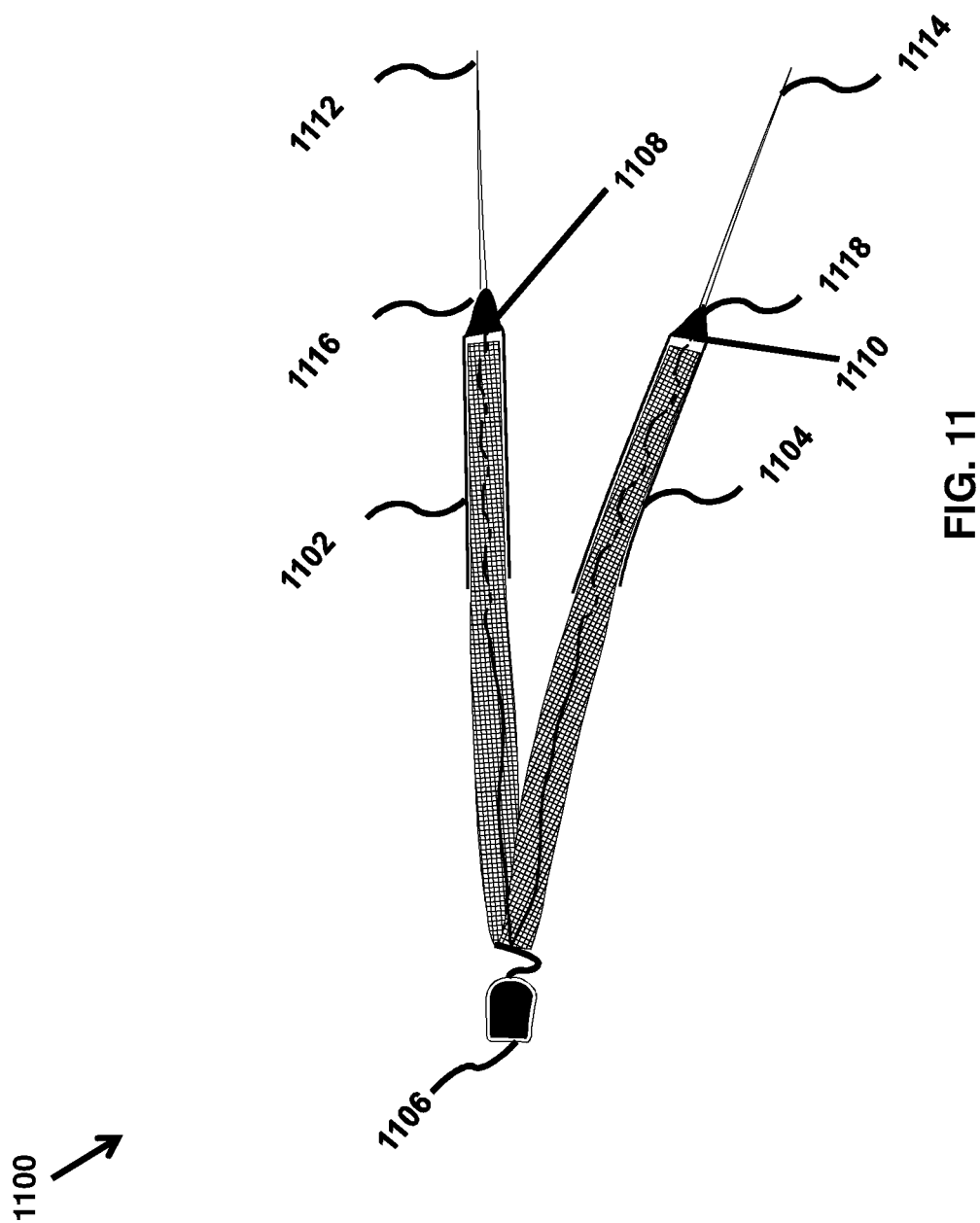
FIG. 11 illustrates a medical assembly including the implant of FIG. 10, in an embodiment of the present invention.

FIG. 11 illustrates a medical assembly in an embodiment. The medical assembly 1100 includes the implant such as 1000, a first sleeve 1102, a second sleeve 1104, a tab 1106, a first elongate member 1108, and a second elongate member 1110. The first sleeve 1102 and the second sleeve 1104 are configured to shield the first portion 1004 and the second portion 1006 of the implant 1000. In some embodiments, the first sleeve 1102 and the second sleeve 1104 can be thin wall flat tubes. In some embodiments, the first sleeve 1102 and the second sleeve 1104 are made of polymer and may be colored for easy visualization. In other embodiments, the first sleeve 1102 and the second sleeve 1104 can be manufactured from an opaque or a transparent plastic film. The transparent plastic film enables visual examination of the implant 1000. In an example, length of the first sleeve 1102 is sufficient to envelop or shield the first portion 1004 of the implant 1000 and length of the second sleeve 1104 is sufficient to shield the second portion 1006 of the implant 1000. In various embodiments, the first portion 1004 is a first end portion of the implant 1000 and the second portion 1006 is a second end portion of the implant 1000 such that the first sleeve 1102 and the second sleeve 1104 are configured to enclose the first end portion and the second end portion respectively of the implant 1000. In certain embodiments of the present invention, the first and the second sleeves 1102 and 1104 shield only the first portion 1004 and the second portion 1006 of the implant 1000 such that the mid portion 1008 of the implant 1000 remains un-shielded. The un-shielded mid portion 1008 is configured to interact with a bodily tissue upon placement. The length of the implant 1000 that is shielded with the sleeves 1102 and 1104 can vary based on requirements.

The medical assembly 1100 may also include a first dilator 1112 configured to be coupled to the first sleeve 1102, and a second dilator 1114 configured to be coupled to the second sleeve 1104. The first dilator 1112 and the second dilator 1114 are configured to be coupled respectively to distal ends 1116 and 1118 of the first sleeve 1102 and the second sleeve 1104. The first dilator 1112 and the second dilator 1114 may be heat bonded respectively to the first sleeve 1102 and the second sleeve 1104. In some embodiments, the first dilator 1112 and the second dilator 1114 may be further configured to be coupled to a delivery device (not shown). The delivery device can be a medical instrument that can be used to facilitate delivery of the medical assembly 1100 including the implant 1000 within the patient's body. In some embodiments, the first dilator 1106 and the second dilator 1108 can be small in diameter for a less invasive surgery.

The medical assembly 1100 may further include the tab 1106 configured to be coupled to the implant 1000. The tab 1106 is configured to identify the medial portion 1008 of the implant 1000 and provide for equal length of the implant 1000 on either side of a body tissue or organ required to be balanced such as a urethra of the patient. In some embodiments, the tab 1106 can be colored for easy visualization during a surgical procedure.

In certain embodiments, the first elongate member 1108 is configured to removably couple the implant 1000 with the first sleeve 1102 and the second elongate member 1110 is configured to removably couple the implant 1000 with the second sleeve 1104. The first elongate member 1108 and the second elongate member 1110 include one of a thread, a medical suture, a filament, a rope, and the like. The first sleeve 1102 and the second sleeve 1104 may be configured to be removably coupled to the implant 1000 with a single elongate member in other embodiments. The sleeves 1102 and 1104 may be removed from the implant 1000 by pulling the elongate members 1108 and 1110 thereby removing the sleeves 1102 and 1104 from the body after positioning and placement of the implant 1000 in the body at the target site. The sleeves 1102 and 1104 may prevent the implant 1000 from contaminations and thus may prevent the body from infection.

In embodiments, the implant 1000 may include or be coupled to anchors, or tangs or other structures for facilitating positioning and fixation of the implant 1000 with bodily tissues. In some embodiments, the implant 1000 may be fixed to tissues using glue, staples, stitches and the like.

Figure 12:
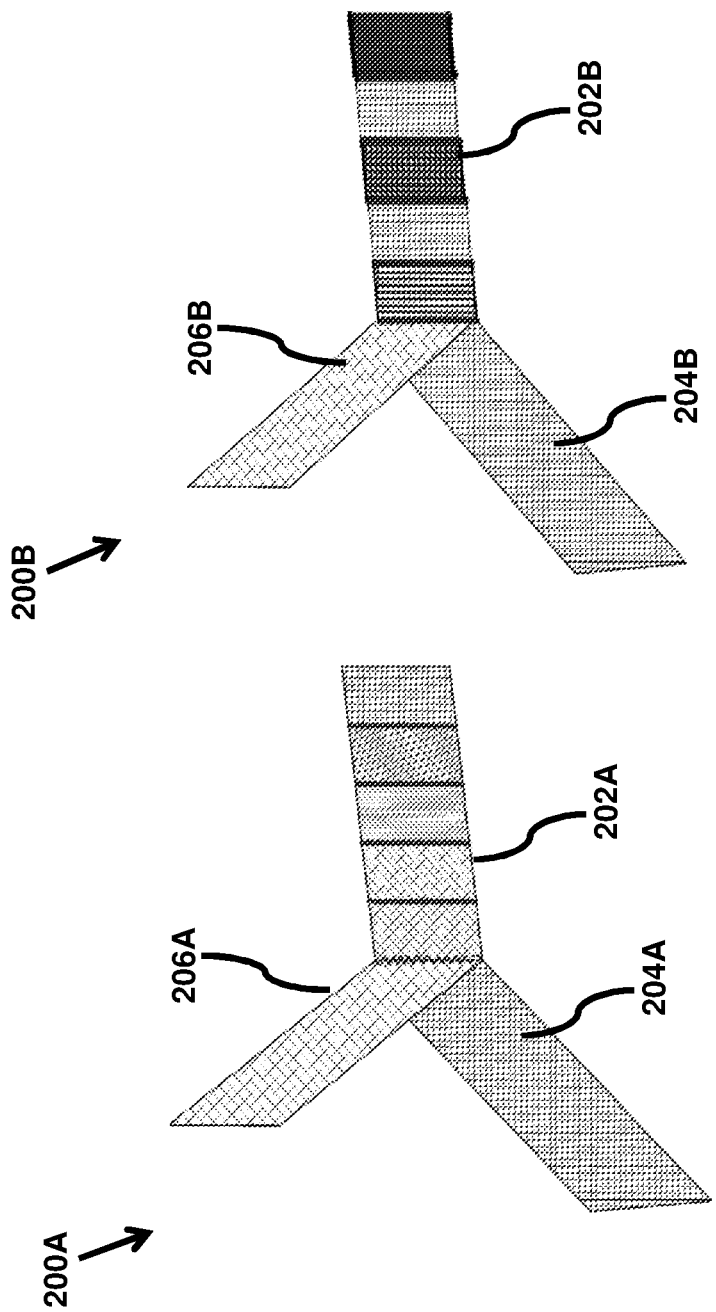
FIG. 12 illustrates schematic diagrams of implants for prolapse repair in accordance with an embodiment of the present invention.

In accordance with various embodiments discussed in conjunction with FIGS. 1-11, the first flap such as 202 or the second flap such as 204 or the third flap such as 206 or the elongate body member 1002 may be defined such as to provide biomechanical characteristics at distinct locations in accordance with biomechanical characteristics of bodily tissues where the respective distinct locations of the first flap 202 or the second flap 204 or the third flap 206 or the elongate body member 1002 may be configured to be attached in association with specific attributes of an individual subject. For example, the first flap 202 of the implant 200 may be configured such that the biomechanical characteristics of the first flap 202 at five distinct locations such as 1-5 may be defined in accordance with the biomechanical characteristics of respective five different locations where these locations of the first flap 202 are configured to be attached in association with specific attributes of the individual subject for which the implant 200 is designed and used. The specific attributes of an individual subject may refer to such as age, unique individual tissue characteristic, and the like without limitations that may result in variations in biomechanical characteristics of even same locations of same tissues between two or more individual subjects. For example, FIG. 12 illustrates two different implants 200A and 200B, wherein 200A is configured to be attached to a first patient and 200B is configured to be associated with a second patient. A first location or region or portion of a first flap 202A of the implant 200A is configured to be attached to a first portion of an anterior vaginal wall of a first subject, a second portion of the first flap 202A of the implant 200A is configured to be attached to second portion of the anterior vaginal wall of the first subject, a third portion of the first flap 202A of the implant 200A is configured to be attached to a third portion of the anterior vaginal wall of the first subject, a fourth portion of the first flap 202A of the implant 200A is configured to be attached to a fourth portion of the anterior vaginal wall of the first subject, and a fifth portion of the first flap 202A of the implant 200A is configured to be attached to a fifth portion of the anterior vaginal wall of the first subject. Similarly, a first portion of a first flap 202B of the implant 200B is configured to be attached to a first portion of an anterior vaginal wall of the second subject, a second portion of the first flap 202B of the implant 200B is configured to be attached to a second portion of the anterior vaginal wall of the second subject, a third portion of the first flap 202B of the implant 200B is configured to be attached to third portion of the anterior vaginal wall of the second subject, and a fourth portion of the first flap 202B of the implant 200B is configured to be attached to a fourth portion of the anterior vaginal wall of the second subject, and a fifth portion of the first flap 202B of the implant 200B is configured to be attached to a fifth portion of the anterior vaginal wall of the second subject. In an example, the first portion of the first implant 200A and the first portion of the second implant 200B may be configured to be attached to almost similar locations of anterior vaginal walls of the two different subjects. Similarly, the second portion of the first implant 200A and the second portion of the second implant 200B may be configured to be attached to almost similar positions of the anterior vaginal walls of the two different subjects, the third portion of the first implant 200A and the third portion of the second implant 200B may be configured to be attached to almost similar positions of the anterior vaginal walls of the two different subjects, the fourth portion of the first implant 200A and the fourth portion of the second implant 200B may be configured to be attached to almost similar positions of the anterior vaginal walls of the two different subjects, and the fifth portion of the first implant 200A and the fifth portion of the second implant 200B may be configured to be attached to almost similar positions of the anterior vaginal walls of the two different subjects. The biomechanical characteristics of the same portions of the vaginal walls of the two different subjects may however vary due to specific individual subject attributes as discussed above. The biomechanical characteristics of the first flap 202A of the first implant 200A and the biomechanical characteristics of the first flap 202B of the second implant 200B may therefore be defined differently in accordance with the biomechanical characteristics of the two different patients using one or more of ways of obtaining desired biomechanical characteristics such as discussed earlier in conjunction with various figures so as to consider variations due to individual subject attributes. For example, FIG. 12 shows that knit pattern or pore sizes or orientation or fabrication material of the first location of the first flap 202A of the first implant 200A is different than knit pattern or pore sizes or orientation or fabrication material of the first location of the first flap 202B of the second implant 200B. Similarly, patterns of other regions or locations of the two implants 200A and 200B may be configured differently so as to define required biomechanical characteristics. In accordance with an exemplary embodiment, FIG. 12 is discussed with respect to variations in biomechanical characteristics of the first flap 202A of the first implant 200A and the first flap 202B of the second implant 200B. Similarly, a second flap 204B of the first implant 200A and a second flap 204B of the second implant 200B; and a third flap 206A of the first implant 200A and a third flap 206B of the second implant 200B may also be configured differently for the two different subjects or even more subjects in accordance with individual subject attributes.

In an aspect, the individual specific attributes may be represented through a set of numerical values that may be determined specifically for each subject. In an aspect, the individual specific attributes may be considered by employing a normalization factor for each attribute during configuring and design of an implant such as the implant 100, 200 or 200A or 200B discussed in conjunction with various figures above.

Therefore, the first flap 202A of the first implant 200A may include a plurality of locations or regions such that biomechanical characteristics at each of the locations or along each of the regions are defined in accordance with respective arbitrary selectable locations at the anterior vaginal wall where the plurality of locations or regions of the first flap are configured to be attached to. The biomechanical characteristics at the plurality of locations or along the plurality of regions may be defined by using one of the several ways as discussed above. The biomechanical characteristics of the arbitrary selectable locations can be dependent on spatial coordinates along the anterior vaginal wall and specific individual subject attributes. Similarly, the second flap 204A of the first implant 200A may include a plurality of locations or regions such that biomechanical characteristics at each of the plurality of locations or along each of the plurality regions are defined in accordance with respective arbitrary selectable locations at the posterior vaginal wall where the plurality of locations or regions of the second flap are configured to be attached to. The biomechanical characteristics at the plurality of locations or along the plurality of regions may be defined by using one of the several ways as discussed above. The biomechanical characteristics of the arbitrary selectable locations can be dependent on spatial coordinates along the posterior vaginal wall and specific individual subject attributes. In a similar manner, the third flap 206A of the first implant 200A may be configured in accordance with some embodiments. Similarly, implants of various other shapes such as the implant 1000 with the elongate body member 1002 of FIGS. 10 and 11 without limitations may also be configured accordingly in a similar manner such that for example, the biomechanical characteristics of a plurality of locations or a plurality of regions on the elongate body member 1002 may be defined in accordance with arbitrary selectable locations or regions of the bodily portion where the medial portion 1008 of the elongate body member 1002 is configured to be attached to as discussed in conjunction with FIGS. 10 and 11.

Figure 13A:
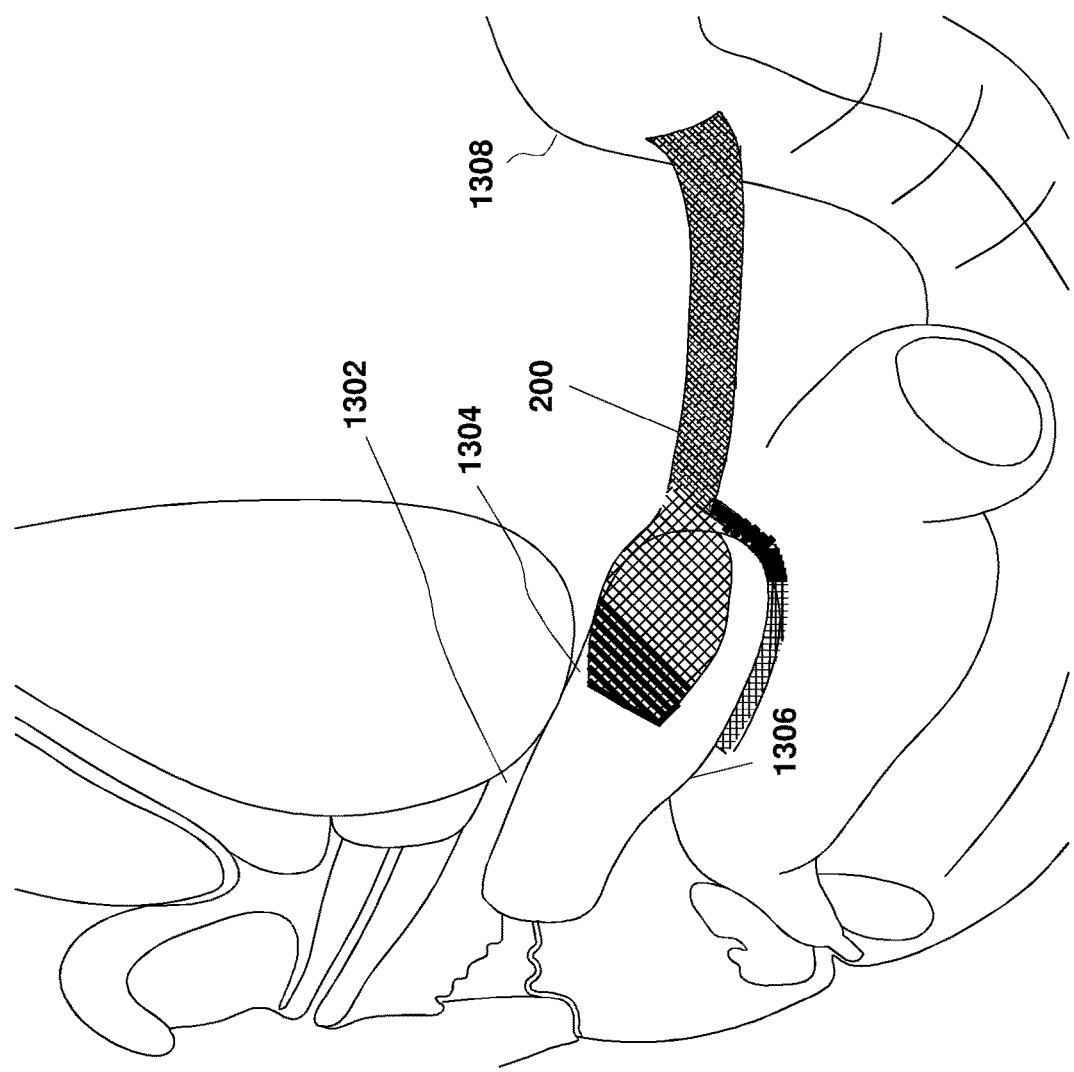
FIGS. 13A and 13B illustrate surgical placement of implants in accordance with exemplary embodiments of the present invention.
Figure 13B:
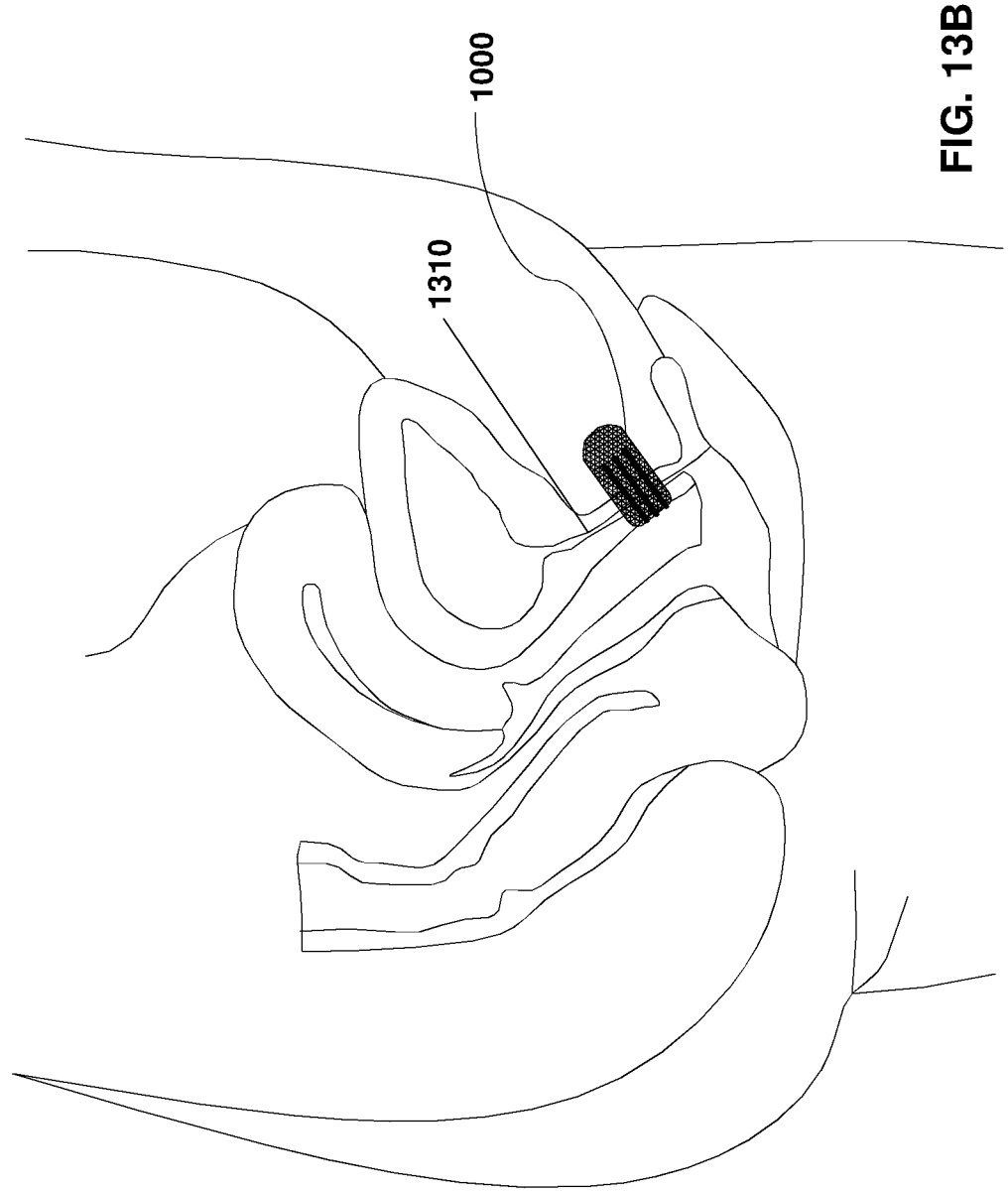

FIG. 13A illustrates a perspective view of an implant such as the implant 100 or 200 or 200A or 200B of FIGS. 1-9, and 12 placed inside a patient's body, in accordance with an embodiment of the invention. FIG. 13B illustrates a perspective view of an implant such as the implant 1000 of FIGS. 10 and 11 placed inside a patient's body, in accordance with an embodiment of the invention. The body portions of the patient such as vagina 1302, anterior vaginal wall 1304, posterior vaginal wall 1306, sacrum 1308, and urethra 1310 are illustrated in FIGS. 13A and 13B.

Figure 14:
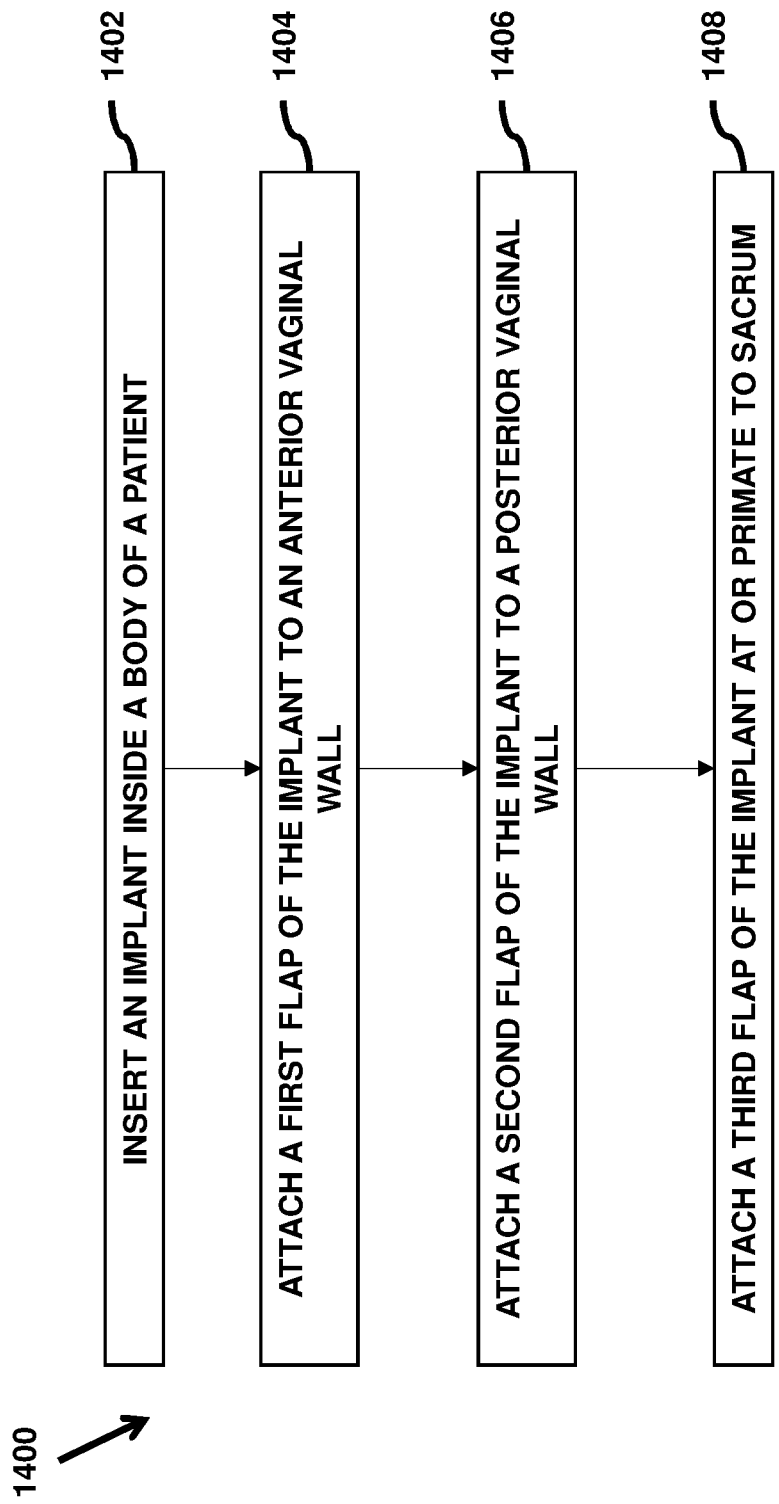
FIG. 14 illustrates a method of delivering and surgically placing an implant for prolapse repair in accordance with an embodiment of the present invention.

FIG. 14 illustrates a method 1400 for placing an implant such as the implant 200 in a patient's body. The method 1400 is described below in conjunction with FIGS. 13A and 13B, as an example without limitations. The implant 200 is used as an exemplary embodiment to illustrate and discuss the method 1400. However, it must be appreciated that other implants such as the implant 100 or 200A or 200B can also be employed without limitations.

The method 1400 may include inserting the first flap 202 of the implant 200 inside the body of a subject at step 1402. In some embodiments, the first flap 202 can be inserted inside the patient's body through a laparoscopic approach. In some embodiments, the method 1400 includes creating an abdominal incision such that the implant 200 can be delivered inside the body using a laparoscopic approach.

The method 1400 may include attaching the first flap 202 of the implant 200 to the anterior vaginal wall 1304 at step 1404. The first flap 202 may be configured in accordance with the anterior vaginal 1304 wall of a specific subject. The method 1400 further includes attaching the second flap 204 of the implant 200 at the posterior vaginal wall 1306 at step 1406. The second flap 204 may be configured in accordance with the posterior vaginal wall 1306.

The method 1400 further includes attaching the third flap 206 of the implant 200 at the sacrum 1308 or proximate tissues inside the patient's body at step 1408.

In some embodiments, the method 1400 can be used for treatment of a pelvic floor disorder. For example, the implant 200 may be used for vaginal prolapse treatment to suspend the vagina 1302 to the sacral promontory or the sacrum 1308 after hysterectomy through the Sacrocolpopexy procedure or without hysterectomy or through any other procedure. In other embodiments, the method 1400 may be used to treat other disorders. In some embodiments, the method 1400 may include creating an abdominal incision or multiple abdominal incisions for delivering the implant 200 inside the body laparoscopically. In an embodiment, the method 1400 may include creating vaginal and/or groin incisions for delivering the implant 200 through other procedures. In an embodiment, the method 1400 may include cutting unneeded portions of the flaps 202, 204, and 206 or sutures after the procedure is complete and removing the unneeded material. In an embodiment, the method 1400 may include attaching the flaps 202, 204, and 206 to bodily tissues using sutures, staples, anchors, bonding agents such as glues, mechanical staplers, or in any other manner. The method 1400 includes closing the incisions after the procedure is complete.

In some embodiments, the procedure of placing the implant 200 within the body can be performed after performing hysterectomy and removal of uterus from the body. In some other embodiments, the implant 200 can be placed even without removing the uterus and the uterus can remain as such.

Figure 15:
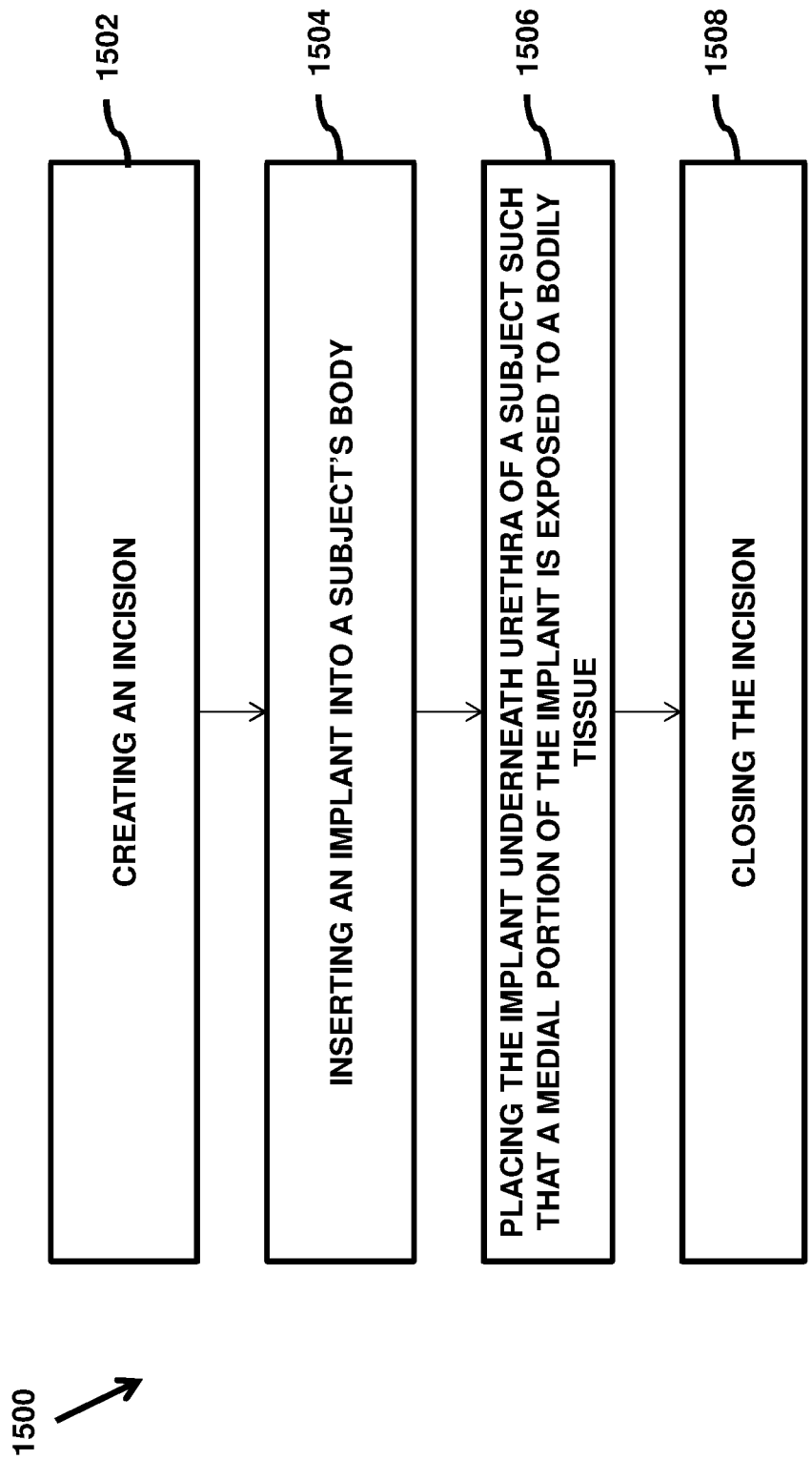
FIG. 15 illustrates a method of delivering and surgically placing an implant for incontinence repair in accordance with an embodiment of the present invention.

FIG. 15 illustrates a method 1500 for placing an implant such as the implant 1000 in a patient's body in accordance with an embodiment. The method 1500 is described herein in conjunction with FIGS. 13A and 13B. As illustrated, the implant 1000 is positioned underneath urethra for providing a support to sub-urethral tissues to prevent leakage of urine due to incontinence in particular stress urinary incontinence. The method 1500 may include creating a vaginal incision or an abdominal incision at step 1502. The method 1500 further includes inserting the implant 1000 inside the patient's body at step 1504. The different portions of the elongate body member 1002 or the medial portion 1008 may behave in accordance with the respective different portions of the sub-urethral tissues where the medial portion 1008 is configured to be attached. After inserting the implant 1000 inside the patient's body, the implant 1000 is placed underneath the urethra (or the bladder neck in other embodiments) of the patient at step 1506 such that the medial portion 1008 of the elongate body member 1002 that is exposed to a bodily tissue contacts the bodily tissue. In an embodiment, the first portion 1004 and the second portion 1006 may be covered by sleeves, such as the sleeves 1102 and 1104 so that only the medial portion 1008 may contact the bodily tissue directly.

In some embodiments, the position of the implant 1000 may be adjusted. The implant 1000 is adjusted in a manner that the implant 1000 contours an outer surface of the urethra that is in contact with the implant 1000. The physician may further adjust tension of the implant 1000 to readjust the implant 1000 to provide it an appropriate tension for effective placement and treatment. The tensioning of the implant 1000 may require stretching of the implant 1000. After tensioning the implant 1000, the method 1500 may further include removing the sleeves 1102 and 1104.

In accordance with some embodiments, the method 1500 further includes trimming a portion of the implant 1000. The trimmed portion can be tucked to the bodily tissues under skin ore removed from the body. In accordance with various embodiments, incisions such as vaginal incision, groin incisions, abdomen incision, or any other skin incision are closed at step 1508.

In various embodiments, exemplary ways of defining or obtaining desired biomechanical characteristics of the flaps such as but not limited to 202, 204, and 206 of the various types of implants such as but not limited 200 discussed in the document are provided elsewhere in the document in conjunction with various figures. Some of them are discussed herein without limitations. It must be however appreciated that more ways of defining the biomechanical characteristics or varying the biomechanical characteristics of the flaps 202, 204, and 206 according to requirements can be used without limitations. The biomechanical characteristics of the elongate body member 1002 may also be defined accordingly using one or a combination of these ways.

In some embodiments, filaments or fibres of the flaps 202, 204, and 206 may be treated with adhesives or bending agents. In an embodiment, the fibres or filaments may be welded to adjacent filaments.

In some embodiments, different materials may be used to form different portions or locations of the flaps or different flaps 202, 204, and 206 such that the different materials may provide different characteristics to the different portions of the implant 200 or to different flaps 202, 204, and 206 of the implant 200.

In some embodiments, the different locations or portions of the implant flaps 202, 204, and 206 or different flaps 202, 204, and 206 may include different number of filaments.

In some embodiments, the different locations or portions of the flaps 202, 204, and 206 or the different flaps 202, 204, and 206 may include different weave patterns.

In some embodiments, the different locations or portions of the flaps 202, 204, and 206 or the different flaps 202, 204, and 206 may include different knit patterns.

In some embodiments, the different locations or portions of the flaps 202, 204, and 206 or the different flaps 202, 204, and 206 may include a coating or multiple types of coatings such as for example a silicone coating so as to vary elasticity or other biomechanical characteristics.

In some embodiments, the different locations or portions of the flaps 202, 204, and 206 or the different flaps 202, 204, and 206 may be annealed or softened or hardened using various mechanical or chemical processes with respect to other portions of the flaps 202, 204, and 206 or with respect to other flaps 202, 204, and 206.

In some embodiments, the different locations or portions of the flaps 202, 204, and 206 or the different flaps 202, 204, and 206 may be contacted with heat, radiation, or treated with chemicals or other agents for providing different characteristics.

In some embodiments, the different locations or portions of the flaps 202, 204, and 206 or the different flaps 202, 204, and 206 may include reinforcing members or different types of reinforcing members.

In some embodiments, the different locations or portions of the flaps 202, 204, and 206 or the different flaps 202, 204, and 206 may include flat or planar sheets of material. The sheets of material may have different pore quantities or distributions to provide different characteristics at different portions of the flaps 202, 204, and 206 or in different flaps 202, 204, and 206.

In some embodiments, the different locations or portions of the flaps 202, 204, and 206 or the different flaps 202, 204, and 206 may include different types of laminated materials or different types of laminations.

In some embodiments, the different locations or portions of the flaps 202, 204, and 206 or the different flaps 202, 204, and 206 may be weakened to provide different characteristics. For example, in some embodiments, portions of the flaps 202, 204, and 206 or different flaps 202, 204, and 206 may be notched, scored, or shaved to introduce weakness or to weaken different portions of the implant 200.

In accordance with some embodiments, the shapes of the first flap 202 and the second flap 204 may be different based on anatomical shapes of the anterior vaginal wall and the posterior vaginal wall.

In some embodiments, different knit structures of the flaps 202, 204, and 206 or different portions of the same flap 202, 204, or 206 can be defined by different pore constructs. For example, the different pore constructs may include different types of pores. In some embodiments, this may be obtained such as by weaving a mesh with different pore sizes and the like. In some embodiments, this may be obtained by extruding a single pore size mesh and heat setting the pores to set a different pore size.

In some embodiments, one or more of the biomechanical characteristics can be defined by a material used for fabricating the flaps 202, 204, and 206 or different portions of the same flap 202, 204, or 206. For example, a viscoelastic medical grade polymer may be used for viscoelasticity effects. In some embodiments, an anisotropic medical grade polymer may be used for obtaining desired anisotropicity in the flaps or different portions of the same flap 202, 204, or 206. In some embodiments, a creep resistant medical grade polymer may be used for a desired creep resistance.

In an example, an imaging device may be used to develop a biomechanical characteristics pattern of bodily tissues such as the sub-urethral fascia or bladder neck or vaginal walls or other tissues. The various implants discussed above may be configured to define a continuous gradient of varying biomechanical characteristics along the flaps 202, 204, and 206 or elongate body member 1002 or along the medial portion 1008 of the elongate body member 1002 in accordance with the biomechanical characteristics pattern of the bodily tissues such that the implant 200 behaves in accordance with the biomechanical behaviour of the bodily tissues. In an example, the pattern or characteristics of the implant 200 may vary throughout the elongate body member 1002 or the flaps 202, 204, and 206 in multiple directions in accordance with a desired gradient of varying biomechanical characteristics at different locations. The flaps 202, 204, and 206 or the elongate body member 1002 may be configured, designed and fabricated using computer assisted designing, modeling, and fabrication methods. Exemplary methods and systems are discussed alter in conjunction with subsequent figures in the document without limitations.

Figure 16:
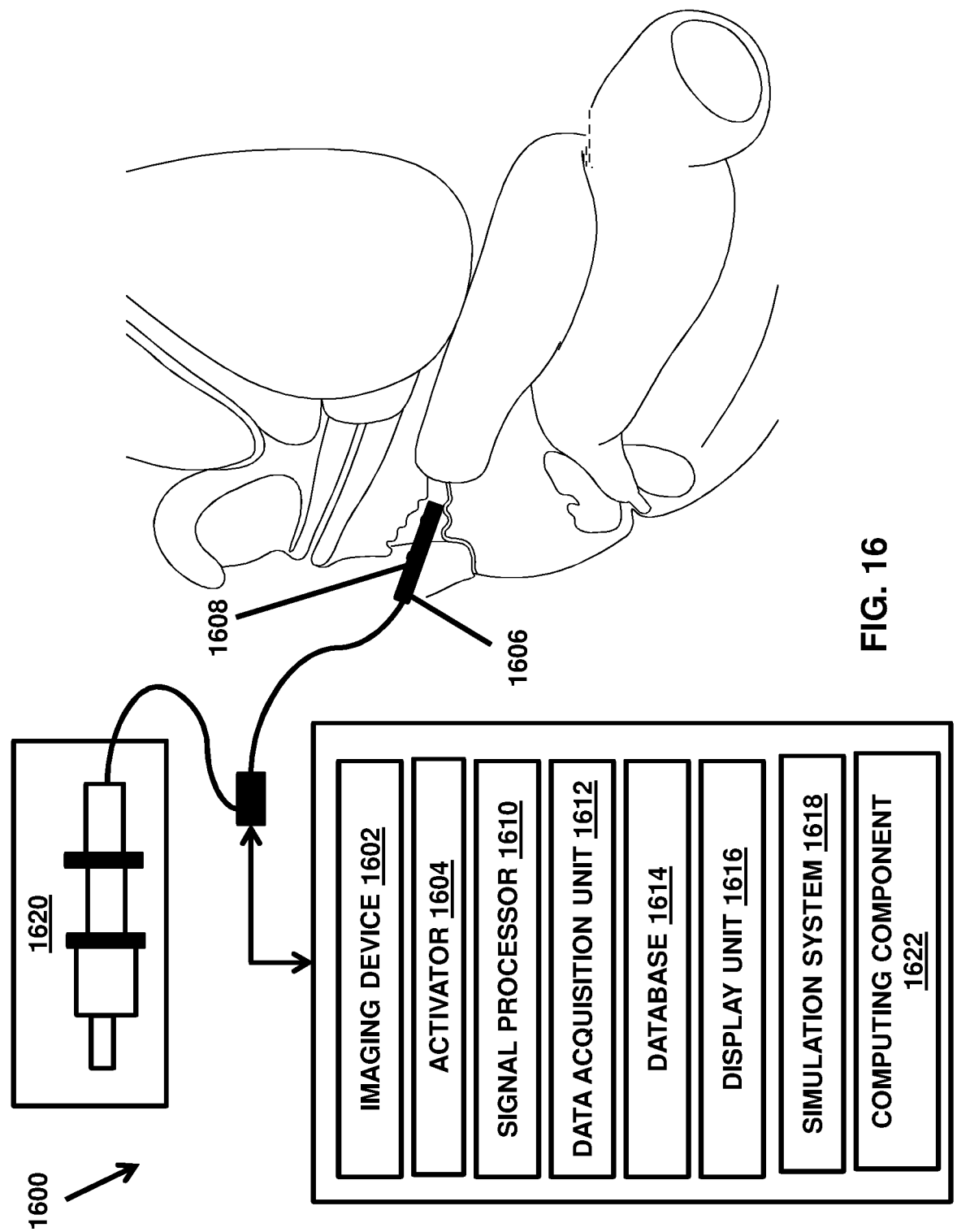
FIG. 16 illustrates a device for determining biomechanical characteristics of bodily tissues and generating a biomechanical characteristic pattern of an implant, in accordance with an embodiment of the present invention.

In accordance with various embodiments, the biomechanical characteristics of the different locations or regions or portions or at arbitrary selectable locations or along a space gradient (indicative of change in variations of biomechanical properties or characteristics with every change in space coordinate) on a vaginal wall, sub-urethral tissues or bladder neck tissues or any other tissues may be determined using a variety of imaging, modeling and/or testing procedures involving use of simulation systems, modeling systems, computing systems, intelligent devices, sensors, programmers, software and the like that may together be referred to as a biomechanical pattern recognition device 1600 such as shown in FIG. 16. It must be appreciated that the biomechanical pattern recognition device 1600 may be used to determine patterns of various localized biomechanical characteristics or average biomechanical characteristics on a portion or region of tissues. In an example, the biomechanical characteristics at a bodily tissue may vary at every next point or every next location of the bodily tissue which can be represented through the biomechanical characteristic pattern that indicates variations of the biomechanical characteristics at different arbitrary selectable locations. The implant 200 or 1000 or any other implant as discussed above may be configured according to the biomechanical characteristics pattern such that at every next point or arbitrary selectable location on the implant 200 or 1000, the biomechanical characteristics may vary depending on the biomechanical characteristics pattern of the bodily tissue. The every next point may be approximated to as every next pore of a mesh-based implant 200 or 1000 in an embodiment so as to vary characteristics, constructs or materials or other parameters of the implant 200 or 1000 at every pore.

FIG. 16 shows the biomechanical pattern recognition device 1600 in an embodiment of the present invention that can be used to determine biomechanical properties of internal tissues of a body. The biomechanical pattern recognition device 1600 can be used to measure biomechanical properties or characteristics inside the vagina of a female. However, the biomechanical pattern recognition device 1600 may be used to determine biomechanical properties of any other internal tissues or organs. In an embodiment, the biomechanical pattern recognition device 1600 can be used to determine stress-strain relationships. In an embodiment, the biomechanical pattern recognition device 1600 can be used to determine viscoelasticity. In an embodiment, the biomechanical pattern recognition device 1600 can be used to determine various other biomechanical characteristics as discussed earlier. The biomechanical pattern recognition device 1600 can determine biomechanical characteristics at arbitrary selectable locations and generate a characteristic pattern or profile indicative of the biomechanical characteristics at the arbitrary selectable locations. The characteristic pattern may be generated in the form of a contour diagram, scatter diagram, heat map, distribution pattern, line diagrams, or in various other formats without limitations. In an example, the biomechanical pattern recognition device 1600 can generate specific numeric values indicative of biomechanical properties or variations in the biomechanical properties at the arbitrary selectable locations. The biomechanical pattern recognition device 1600 may include an imaging device 1602, an activator 1604, a probe 1606, sensors 1608 coupled to the probe 1606, a signal processor 1610, a data acquisition unit 1612, a database 1614, and a display unit 1616. The probe 1606 can be inserted inside the vaginal opening in an example. The activator 1604 may perform an action that initiates an action to cause a change in the tissues such as vaginal walls at the arbitrary selectable locations. For example, the activator 1604 can apply a deforming force in order to determine stress-strain relationships or to determine elasticity or hyperelasticity, in an embodiment. In another embodiment, the activator 1604 can apply a chemical spray at the arbitrary selectable location so as to detect a response indicative of change in viscoelasticity or viscosity. In some embodiments, the activator 1604 can be of various types or can include a combination thereof so as to determine various types of biomechanical properties. The imaging device 1602 may detect the changes and responses at the arbitrary selectable locations after the activator 1604 performs the action. For example, in an embodiment, the imaging device 1602 may detect dimensional changes, viscoelasticity changes, and the like. The data acquisition unit 1612 may receive the response and signals indicative of the changes obtained by the imaging device 1602. The data acquisition unit 1612 may be coupled communicatively with the signal processor 1610 or any other processing circuit so as to correlate the responses with the action and generate an output indicative of the biomechanical characteristic pattern or biomechanical characteristics measurements at the arbitrary selectable locations. The output may be represented on the display unit 1616 such as a screen, monitor, or any other device.

The biomechanical pattern recognition device 1600 may include a simulation system 1618. The simulation system 1618 may be configured to simulate interactions between the tissues and the implant such as 200 or implant portion. The simulation system 1618 may further be configured to generate biomechanical data and behaviour of the tissues such as the vaginal walls if a specific implant with specific biomechanical characteristics at the arbitrary selectable locations for a specific individual is positioned. The simulation system 1618 may allow modifying parameters of the implant 200 at the different arbitrary selectable locations based on the generated biomechanical data so as to define the implant 200 in such a way that the biomechanical behaviour of the implant 200 at the arbitrary selectable locations is in accordance with the tissues or regions where the arbitrary selectable locations of the implant 200 are configured to be placed. The simulation system 1618 may generate a realistic simulation environment for various tissues where the implant is attached. The simulation system 1618 provides a user with a capability to define implant parameters accordingly and to generate modeling interactions. The simulation system 1618 may facilitate to generate the biomechanical characteristics pattern or biomechanical characteristics at the arbitrary selectable locations without actual in vivo procedures performed such as with the help of the activator 1604 and probe 1606. In such an embodiment, the simulation system 1618 may store geometric models of bodily tissues or organs and other pertinent details in a database. The simulation system 1618 may be provided with specific patient attributes so as to generate and determine the biomechanical characteristics of a specific person at the arbitrary selectable locations by correlating different data elements associated with tissue characteristics as obtained from the database 1614 and patient specific attributes as received from a user input.

Therefore, as discussed above, in conjunction with various embodiments, the biomechanical characteristics (or patterns or profiles) at the arbitrary selectable locations may be determined using either in vivo actual tests, ex vivo actual test, or simulation and modeling interactions with the help of realistic simulation environment. The biomechanical pattern recognition device 1600 may include computer aided designing and analytics software packages. The biomechanical pattern recognition device 1600 may further include various other components and sub-components such as power supply, mechanical arrangements or components, circuitry, wires, other electronic or electrical components and auxiliary components together shown as 1620 to determine the biomechanical characteristics.

In an embodiment, the biomechanical pattern recognition device 1600 may include a pressure unit (not shown) for applying a defined pressure to an arbitrary selectable location of a bodily tissue. A sensor may detect a deformation caused by application of the defined pressure.

In an example, different biomechanical pattern recognition devices may be used for determining different types of properties. For example, strength or strength patterns may be determined using a first device while elasticity or elasticity patterns may be determined using another device. In some embodiments, the same biomechanical pattern recognition device 1600 may be used to determine various characteristics such that the biomechanical pattern recognition device 1600 may involve multiple sub-components each configured to determine a specific biomechanical property or characteristic. The biomechanical pattern recognition device 1600 may in such a case generate an output in the form of a series of values indicative of measures of biomechanical characteristics at different regions or portions or locations corresponding to each characteristic or a set of patterns with each pattern indicative of distribution of a specific biomechanical characteristic.

In an embodiment, the biomechanical pattern recognition device 1600 may determine the biomechanical characteristics in vivo. In an embodiment, the biomechanical pattern recognition device 1600 may determine the biomechanical characteristics from sample tissues such that output and findings may be used to extrapolate it for generating characteristics or characteristic patterns of specific test group. For example, the biomechanical pattern recognition device 1600 may determine characteristics or characteristic patterns at arbitrary selectable locations or such as along an entire anterior vaginal wall of specific age group tissues such that an output of the biomechanical pattern recognition device 1600 may be indicative of fairly accurate representation of various biomechanical characteristics at different arbitrary selectable locations or along an entire vaginal wall of even another subject with age similarities with the test group. In another example, however, in vivo measurements may be taken to customize implant design and fabrication for specific tissues, tissue locations, and for specific subjects.

In an embodiment, the biomechanical pattern recognition device 1600 may measure the biomechanical characteristics by applying a temporary deforming force at an arbitrary selectable location of tissues such as vaginal wall tissues, or other pelvic tissues. The deforming force may be applied through vacuum suction or air pressure or rotational torsion, tissue stretching, or striking the location with an object, and the like. The biomechanical pattern recognition device 1600 may evaluate how the tissue responds in response to the applied force as well as how it responds after the deforming force is removed. The biomechanical pattern recognition device 1600 may use sensors to detect the response during application of the force and after the force is removed. By monitoring the response at the arbitrary selectable location, the biomechanical pattern recognition device 1600 may generate a characteristic pattern indicative of biomechanical characteristics at the arbitrary selectable location or region within and around the arbitrary selectable location. The biomechanical pattern recognition device 1600 may include a computing component 1622 operably and communicatively connected with the probe 1606 such that the probe 1606 may be inserted into the vagina and record the response upon application of the force. The response may then be evaluated by the computing component 1622. The computing component 1622 may record the deforming force and the response detected by the sensors 1608 that may be coupled to the probe 1606. The probe 1606 may include sensors such as laser-based sensors, temperature-based sensors, mechanical sensors, ultrasonic sensors, pressure sensors, ultrasound-based sensors, and the like without limitations.

The computing component 1622 may be configured to define an implant pattern based on the biomechanical characteristic pattern of the bodily tissue. The implant pattern may identify parameters of the implant at various arbitrary selectable locations defined in a way that the biomechanical characteristics of the implant 202 at the arbitrary selectable locations are in accordance with the biomechanical characteristics of the bodily tissue. The implant parameters may include such as pore size, pore shape, material of fabrication, knit pattern and the like as discussed elsewhere in the document without limitations. For example, the computing component 1622 may be configured to develop implant pattern of the first flap 202 and the second flap 204 of the Y-shaped implant 202 (or other implants as discussed above in conjunction with various figures) based on a biomechanical characteristic pattern of respective posterior vaginal wall and anterior vaginal wall, wherein the first flap 202 is adapted to be attached to the anterior vaginal wall and the second flap is adapted to be attached to the posterior vaginal wall.

In an embodiment, the biomechanical pattern recognition device 1600 may determine the biomechanical characteristics or characteristic patterns using a dynamic optical coherence elastography technique. The biomechanical pattern recognition device 1600 may determine the biomechanical characteristics based on mechanical surface wave propagation that may allow determination of the biomechanical characteristics at the arbitrary selectable locations in vivo in different orientations and different directions. In some embodiments, the biomechanical characteristics may be determined through optical imaging techniques such as optical elastography, optical sensing and imaging, optical coherence elastography, multiphoton electrography, magnetomotive microscopy; vaginal tactile imaging, ultrasound elastography; cross-sectional imaging-based elastography; MRI elastography; MRI, 2-D or 3-D imaging, optical scattering variations, biomedical imaging, diffraction phase microscopy, micro-scale mapping, tensile tests, digital image correlation, statistical analysis, deformation tests, mechanical imaging such as tactile imaging, stress imaging and the like, 2-D or 3-D image reconstruction, or any other technique without limitations for determining various types of biomechanical properties. In an embodiment, mechanical imaging may be employed to generate biomechanical characteristic pattern or profiles for vaginal walls. For example, the biomechanical pattern recognition device 1600 may include a transvaginal probe such as the probe 1606, an electronic unit, and a computing device. The vaginal probe may include sensors similar to the sensors 1608.

It must be appreciated that the biomechanical pattern recognition device 1600 discussed herein can be used in an exemplary embodiment. However, several other types of pattern recognition systems or devices to determine biomechanical characteristics may be employed without limitations.

In accordance with some embodiments, the biomechanically compatible implant discussed throughout the document, number of arbitrary selectable discrete locations on each flap or on an elongate body member may be at least fifty such that the biomechanical characteristics at the arbitrary selectable at least fifty discrete locations of the flap or the elongate body member of the implant varies in accordance with variations in the biomechanical characteristics of the arbitrary selectable at least fifty discrete locations of the anterior vaginal wall or posterior vaginal wall or sub urethral tissues. In accordance with some embodiments, the biomechanically compatible implant discussed throughout the document, number of arbitrary selectable discrete locations on each flap or on an elongate body member may be at least five such that the biomechanical characteristics at the arbitrary selectable at least five discrete locations of the flap or the elongate body member of the implant varies in accordance with variations in the biomechanical characteristics of the arbitrary selectable at least five discrete locations of the anterior vaginal wall or posterior vaginal wall or sub urethral tissues. In an example, the at least one of the arbitrary selectable five or fifty discrete locations extends along a partial length of the first flap or the second flap or the elongate body member. In an example, the at least one of the arbitrary selectable five or fifty discrete locations extends along a partial width of the first flap or the second flap or the elongate body member. The biomechanical characteristics of the first flap or the second flap or the elongate body member at the arbitrary selectable discrete locations are defined based on an input signifying age, pregnancy or childbirth state, intra-abdominal forces interactions, and state of prolapse associated with a subject and the like.

Figure 17:
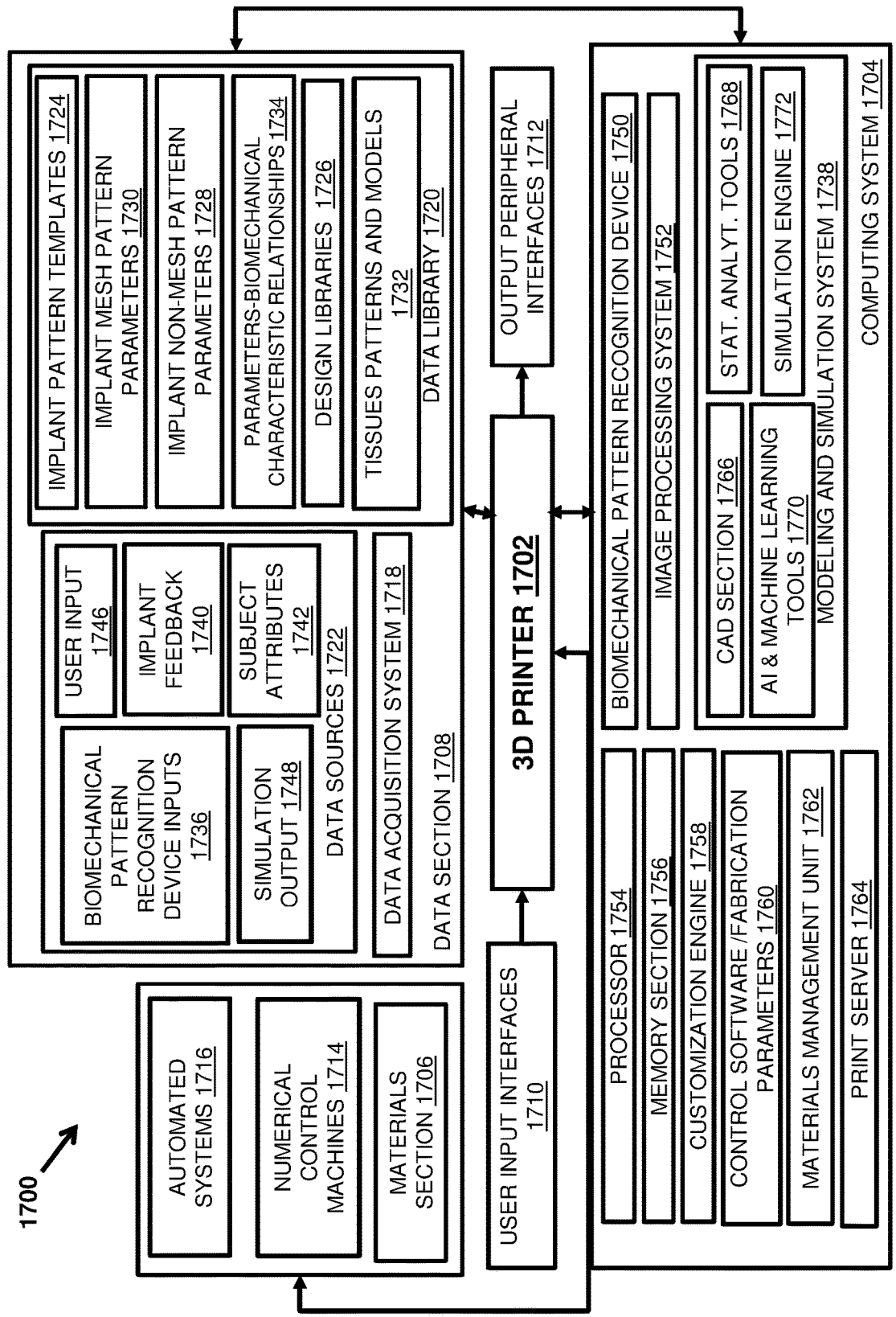
FIG. 17 illustrates a system for designing and/or fabricating an implant, in accordance with an embodiment of the present invention.

FIG. 17 illustrates a 3D (three dimensional) printing ecosystem 1700 (or system 1700) for fabrication of an implant such as the implant 200 or other implants discussed in accordance with various embodiments above, in an embodiment of the present invention. The system 1700 may include a 3D printer (also referred to as additive manufacturing device) 1702, a computing system 1704, a materials section 1706, a data section 1708, user input interfaces 1710, output peripheral interfaces 1712, numerical control machines 1714, and other automated systems 1716.

The 3D printer 1702 may be configured to perform one or more additive fabrication or layered manufacturing processes to manufacture a customized and smart implant such as the implant 200 that mimics behaviour of tissues where the implant is configured to be attached wherein biomechanical characteristics of the implant 200 at arbitrary selectable locations after fabrication and when placed within the body are in accordance with biomechanical characteristics at arbitrary selectable locations of the tissues where the respective arbitrary selectable locations of the implant 200 are placed.

In accordance with an embodiment, the 3D printer 1702 may be configured to execute fused deposition modeling (FDM)™ processes. The process of FDM™ may involve a software process which may process an STL (stereolithography) file or any other file format. The STL file may for example contain details about the biomechanical characteristic pattern of the tissues at the arbitrary selectable locations or implant biomechanical characteristic pattern based on the biomechanical characteristic pattern of the tissues. An object may be produced by extruding small beads of for example thermoplastic or any other material to form layers as the material hardens immediately after extrusion from a nozzle. A material filament or wire is unwound from a coil and supplies material to an extrusion nozzle which can turn the flow on and off. A worm-drive or any other drive system may be provided to push the filament into the nozzle at a controlled rate. The nozzle is heated to melt the material. The nozzle can be moved in both horizontal and vertical directions. The nozzle may follow a tool-path controlled by a computer-aided manufacturing (CAM) software package, and the object is fabricated from the bottom up, one layer at a time.

In accordance with an embodiment, the 3D printer 1702 may be configured to execute electron beam freeform fabrication processes. The Electron Beam Freeform Fabrication (EBFFF) process may utilize electron beam welding technology to create parts. In an aspect of the invention, with the EBFFF method, metallic preforms can be manufactured from computer-generated 3D drawings or models. The deposition path and process parameters may be generated from post-processing of a virtual 3D model and executed by a real-time computer control. The deposition takes place in a vacuum environment. A wire may be directed toward the molten pool and melted by a focused EB. Different parts of the object to be fabricated are built up layer by layer by moving the EB and wire source across a surface of underlying material referred to as substrate. The deposit solidifies immediately after the electron beam has passed.

In accordance with an embodiment, the 3D printer 1702 may be configured to execute direct metal laser sintering process (DMLS). DMLS process may involve a laser as a power source to sinter powdered material such as a metal or any other material at points in space defined by a 3D model thus binding the material together to create a solid structure. The DMLS process may involve use of a 3D CAD model whereby a .stl file is created and sent to the 3D printer's software. The DMLS-based 3D printer 1702 uses a high-powered fiber optic laser. The metal powder is fused into a solid part by melting it locally using the focused laser beam. Object parts are built up additively layer by layer.

In accordance with an embodiment, the 3D printer 1702 may be configured to execute selective laser melting (SLM) process. The SLM process uses 3D CAD data as a digital information source and energy in the form of a high-power laser beam to create three-dimensional parts by fusing fine powders together. The process involves slicing of the 3D CAD file data into layers to create a 2D image of each layer. Thin layers of atomized fine powder are evenly distributed using a coating mechanism onto a substrate plate that is fastened to an indexing table that moves in the vertical (Z) axis. This takes place inside a chamber containing a tightly controlled atmosphere of inert gas such as argon. Once each layer has been distributed, each 2D slice of the geometry is fused by selectively applying the laser energy to the powder surface, by directing the focused laser beam using two high frequency scanning mirrors in the X and Y axes. The laser energy permits full melting of the particles to form solid metal. The process is repeated layer after layer until the part is complete.

In accordance with an embodiment, the 3D printer 1702 may be configured to execute selective heat sintering process. The process may involve a thermal printhead to apply heat to layers of powdered thermoplastics or other materials. When a layer is finished, the powder bed of materials moves down and an automated roller adds a new layer of material which is sintered to form a next cross-section of the object.

In accordance with an embodiment, the 3D printer 1702 may be configured to execute selective laser sintering process. The process of selective laser sintering (SLS) involves a laser used to melt a flame-retardant plastic or synthetic material powder, which then solidifies to form the printed layer.

In accordance with an embodiment, the 3D printer 1702 may be configured to execute plaster-based 3D printing processes.

In accordance with an embodiment, the 3D printer 1702 may be configured to execute laminated object manufacturing process. In this process, layers of adhesive-coated material laminates may be successively glued together and cut to shape with a knife or laser cutter.

In accordance with an embodiment, the 3D printer 1702 may be configured to execute stereo-lithography (SLA) processes. The process may employ a vat of liquid ultraviolet curable photopolymer "resin" and an ultraviolet laser to build layers one at a time. For each layer, the laser beam traces a cross-section of the part pattern on the surface of the liquid material. Exposure to the ultraviolet laser light cures and solidifies the pattern traced on the resin and joins it to the layer below.

In accordance with an embodiment, the 3D printer 1702 may be configured to execute digital light processing (DLP) methods. Digital Light Processing uses a projector to project an image of a cross section of an object into a vat of photopolymer (light reactive plastic). The light selectively hardens only the area specified in that image. A printed layer is then repositioned to leave room for unhardened photopolymer to fill newly created space between the print and the projector. Repeating this process builds up the object one layer at a time.

In accordance with an embodiment, the 3D printer 1702 may be configured to execute photopolymerization methods. In this process, drops of a liquid plastic or other synthetic material are exposed to a laser beam of ultraviolet light. During this exposure, light converts the liquid into a solid.

In accordance with some embodiments, the 3D printer 1702 may involve use of an inkjet type printhead to deliver a liquid or colloidal binder material to layers of a powdered build material. The printing technique may involve applying a layer of a powdered build material to a surface such as using a roller. After the build material is applied to the surface, the printhead delivers the liquid binder to predetermined areas of the layer of material. The binder infiltrates the material and reacts with the powder, causing the layer to solidify in the printed areas by, for example, activating an adhesive in the powder. After the first cross-sectional portion is formed, the steps are repeated and successive cross-sectional portions are fabricated until the final object is formed.

In an aspect, the methods performed by the 3D printer 1702 may involve deposition of successive layers of a build material on a rotary build table and deposition of a liquid in a predetermined pattern on each successive layer of the build material to form a three-dimensional implant.

The data section 1708 may include various components and sub-components such as a data acquisition system 1718, various data libraries 1720, and data sources 1722, without limitations.

The data acquisition system 1718 may receive or acquire data signal from external or internal environments including the data sources 1722 and convert them into digital information for use by the 3D printer 1702 and the computing system 1704 to process the digital information for manufacturing a three-dimensional implant using the successive layers deposition techniques.

The data section 1708 may include the data libraries 1720 that may contain predefined information for use by the 3D printer 1702 and the computing system 1704 to create custom designed and custom defined implant that exhibit biomechanical characteristics pattern in accordance with biomechanical characteristics pattern of bodily tissues. The data libraries 1720 may include implant pattern templates 1724 that may contain different predefined templates of patterns for a biomechanically compatible implant for use at various bodily tissues such as an anterior vaginal wall, a posterior vaginal wall, sub-urethral facia, bladder neck etc. The predefined implant pattern templates 1724 may be directly used by the 3D printer 1702 to fabricate the implant such as 200, in an embodiment. In another embodiment, the implant pattern templates may be used and modified slightly or substantially in accordance with the digital information acquired through the data sources 1722 to customize the implant 200. The data libraries 1720 may further include design libraries 1726 that may contain three dimensional or two dimensional or CAD designs of various types of implants for use in fabrication. For example, the design library 1726 may store a CAD design or model of a Y-shaped implant such as 200 or a linear strip-based implant such as 1000 with an elongate body member 1002, and the like such that the designs and models of the implants may be refined with the use of the implant pattern templates 1724 for customization of the implant 200 of a specific design with a specific pattern. The data library 1720 may further store implant non-mesh pattern parameters 1728 that may be used to define or vary biomechanical characteristics of a non-mesh-based implant. For example, the non-mesh pattern parameters 1728 may include such as fabrication method, material deposition or layering technique, type of material for fabrication, thickness of deposition material, width, shape, and others such as those discussed elsewhere in the document without limitations. The data library 1720 may further store implant mesh-pattern parameters 1730 that may be used to define or vary biomechanical characteristics of a mesh-based implant. For example, different implant mesh pattern parameters 1730 may include such as pore construct, pore shape, pore size, fibre orientation, and others such as those discussed elsewhere in the document without limitations. The data libraries 1720 may store tissue patterns and models 1732 that may contain digitally maintained information of patterns and models of various bodily tissues and associated biomechanical characteristics at different arbitrary selectable locations or regions. For example, tissue patterns and models 1742 of an anterior vaginal wall may be provided in the data libraries 1720 to define an interactive and user retrievable information base wherein a user of the 3D printer 1702 or the computing system 1704 or various other systems in the ecosystem 1700 may selectably identify and retrieve biomechanical characteristics at arbitrary selectable locations or regions of a bodily tissue. The biomechanical characteristics may be provided to the other components or sub-components for further processing before defining a customized implant and manufacturing thereof through the 3D printer 1702. In an example, the tissues patterns, designs and models 1732 may not represent biomechanical characteristics of a particular individual with complete accuracy but may provide a generic information about how a particular tissue or an arbitrary selectable region or location at the tissue may behave so that this information may be used by the computing system 1704 to further process it for defining a desired design of the implant 200 for an individual or for a particular location or region of the tissue. The data libraries 1720 may further store details about parameters-biomechanical characteristics relationships 1734. The parameters-biomechanical characteristics relationships 1734 may associate relationships between different biomechanical characteristics and various implant parameters such as implant mesh-pattern parameters 1730 and implant non-mesh pattern parameters 1728. For example, the relationships may define how for example elasticity may vary with a change in a specific parameter such as a pore construct etc.

The data sources 1722 may include different information sources or data sources such that the data acquisition system 1718 may operatively and/or communicatively be connected with the data sources 1722 to retrieve the digital information for defining manufacturing inputs provided by the user to the 3D printer 1702 through user input interfaces 1710. The information obtained from the data sources 1722 may be directly provided to the 3D printer 1702, in an embodiment. In another embodiment, the information may be provided to other systems such as the computing system 1704 etc for further processing before being given to the 3D printer 1702. The data sources 1722 may for example include biomechanical pattern recognition device inputs 1736 that may include information or data provided by the biomechanical pattern recognition device 1600 of FIG. 16 or any other recognition device. The biomechanical pattern recognition device inputs 1736 may for example include biomechanical pattern of the tissues and/or biomechanical pattern of the implant at the arbitrary selectable locations or regions. The data sources 1722 may further include user input 1746 that may be entered by the user during operation of the 3D printer 1702 or during accessing different components of the ecosystem 1700 or during manipulating data flow across different components and sub-components. The data sources 1722 may include simulation output 1748 that may include information generated by a modeling and simulation system such as a modeling and simulation system 1738 described later. The data sources 1722 may include implant feedback information 1740 which may be obtained from physicians or doctors or electronic medical records (EMR) after the implant 200 is already delivered and used in a subject's body. The subject may experience the implant 200 and accordingly information based on real experience of the implant 200 by the subject or based on actual behaviour of the implant 200 within bodily tissues may be maintained by the doctor manually or in an EMR. This information may be termed as implant feedback or subject feedback herein. The data sources 1722 may further include subject attributes 1742 that may define specific characteristics or data elements associated with an individual subject which may be used to customize the implant 200 for the specific individual. The subject attributes 1742 may for example include, age, unique individual tissue characteristics, pregnancy state, gender, and other such attributes as mentioned elsewhere in the document.

The user input interfaces 1710 may include input devices such as a keyboard, mouse, touch screen device, interactive or non-interactive user interfaces, graphical input devices, voice recognition systems, and other input devices.

The computing system 1704 may include a biomechanical pattern recognition device 1750, an image processing system 1752, the modeling and simulation system 1738, a processor 1754, a memory section 1756, a customization engine 1758, control software 1760 to control fabrication parameters, a materials management unit 1762, a print server 1764, and various other systems or components or sub-components.

The biomechanical pattern recognition device 1750 may be similar to the biomechanical pattern recognition device 1600. In an embodiment, the pattern recognition device 1750 may be integrated within the ecosystem 1700 such that a separate biomechanical pattern recognition device 1750 may not be needed. The image processing device 1752 may perform processing of scanned or other images or patterns of bodily tissues or implant as obtained or created by the biomechanical pattern recognition device 1750 or other components or systems. The image processing device 1752 may include or be coupled to a scanner or a camera in an embodiment. The materials management unit 1762 may control flow of materials from the materials section in accordance with requirements of different materials in different amounts at different times at different arbitrary selectable locations or regions of the implant 200 during deposition or 3D printing. The different materials or a combination of different materials may contribute to varying biomechanical characteristics of the implant 200 at the different arbitrary selectable locations or regions. The computing system 1704 may include the customization engine 1758 for generating a 3D printable and computer executable file using information generated from various components and sub-components of the ecosystem 1700 and information retrieved from the data sources 1722 so that an output generated by the customization engine 1758 when input into the 3D printer 1702 allows the 3D printer 1702 to fabricate the implant 200 (or 1000 or other implants in various embodiments) with desired patterns at the arbitrary selectable locations in accordance with customized inputs for the customized implant 200. The computing system 1704 may include control software 1760 for controlling materials deposition and other fabrication control parameters during printing processes such that the controlled fabrication or printing by the 3D printer 1702 based on instructions by the control software 1760 fabricates the desired biomechanically compatible implant 200. The computing system 1704 may include the print server 1764 that may be coupled communicatively through a network to various other systems, components and sub-components of the ecosystem 1700 and other remotely located devices or server or other 3D printing ecosystems similar to the 3D printing ecosystem 1700 or a plurality of other 3D printers including printers similar to the 3D printer 1702 without limitations. The print server 1764 may provide a control of the various systems within or outside the ecosystem 1700 over the network and facilitate networking operations among the various devices, systems, components, sub-components of the ecosystem 1700 themselves and/or across other devices, systems, components, sub-components of other ecosystems. The print server 1764 may facilitate an automated fabrication operation of the 3D printer 1702 or several networked 3D printers with minimal or no supervision.

The computing system 1704 may include the processing circuit or the processor 1754 for performing various routine processing and computing activities of the computing system 1704. The processor 1754 may be connected with the memory circuit or memory section 1756 for storing computer executable programmed instructions to execute the processing functions or activities by the processor 1754 or other components or sub-components of the computing system 1704.

The computing system 1704 may further include the modeling and simulation system 1738. The modeling and simulation system 1738 may include a computer aided designing (CAD) section 1766, statistical and analytical tools 1768, artificial intelligence and machine learning tools 1770, a simulation engine 1772 and other components for developing simulation scenarios and generating predictive models based on a simulation output. The CAD section 1766 may include CAD designing tools for developing models of bodily tissues, implant patterns, biomechanical characteristics patterns that may be supplied to the data libraries 1720 or other components of the data section 1708 or to the various components of the computing system 1704 for further processing to develop the computer executable and 3D printable file defining input parameters for fabrication of the 3D printable implant. The file can be a .stl file in an embodiment. In another embodiment, the file can be created in other format. The designs and models developed by the CAD section 1766 may be generated based on a predictive behaviour by creating a real like simulated environment by the simulation engine 1722. The simulation engine 1722 may utilize several statistical and analytical tools, and artificial intelligence and machine learning tools to develop a simulated environment so that behaviour of the implant models or designs may be examined prior to fabrication in accordance with behaviour of the bodily tissues within the body where the implant 200 may be configured to be attached.

The ecosystem 1700 may include the materials section 1706 that may contain a plurality of chambers containing different materials for use in fabrication of the biomechanically compatible implant 200 such that the materials from the different chambers flow in accordance with instructions from the computing system 1704 or the materials management unit 1762 so as to use a combination of materials based on requirements of the materials at the different arbitrary selectable locations or regions of the implant 200 to be fabricated by the 3D printer 1702. The materials section 1706 may include a plurality of sensors operatively or communicatively connected with the materials chambers to control and monitor flow of the materials to the 3D printer 1702 as instructed by the computing system 1704.

The 3D printer 1702 may be communicatively and operatively connected with the numerical control machines (NCM) 1714 and other automated systems such as robots 1716 etc for automatically facilitating other fabrication processes in association with 3D printing or layered deposition.

The printed implant 200 may be received at the output peripheral interfaces 1712 that may include mechanical components for receiving the printed implant 200 or computer interfaces for executing post-printing tasks such as interactive interfaces for reviewing the implant behaviour or examining the printed implant various characteristics and the like.

In accordance with various embodiments of the present invention, 3D (three-dimensional) printing or additive manufacturing or fabrication may be referred to as a manufacturing technique or technology for manufacturing of three-dimensional objects using additive processes such as layered deposition in which successive layers of one or more types of materials are laid down under control of programmed instructions. The 3D printing fabrication technique as discussed above may be employed to manufacture implants or other objects of almost any shape, size, characteristic, geometry, etc. The above embodiment is discussed in conjunction with the implant 200. However, it must be appreciated that other implants such as 100 or 1000 may also be designed and/or fabricated in a similar manner.

In accordance with various embodiments discussed above, the implant 200 may be used for or adapted with slight modifications to be used for urinary incontinence, fecal incontinence, breast implant, hernia, abdominal repair, various types of prolapse, breast uplift, or various other types of treatment options or reconstructive or plastic or artificial tissue growth surgeries, and the like without limitations.

In accordance with various embodiments, the implant discussed in this document provides several advantages. The biomechanically compatible or biomechanically suitable implant is designed and fabricated in accordance with the biomechanical properties or characteristics of bodily tissues and therefore the implant mimics the behaviour of the bodily tissues. This reduces the chances of complex issues that may arise due to rejections of a foreign material such as the implant by a body. For example, since the biomechanical behaviour of the implant is similar to the biomechanical behaviour of the bodily tissue, there is a reduced chance of issues such as contraction, extrusion, erosion of the implant. Further, the chances of infection can be reduced. Further, a customized implant manufactured through an additive process such as buy the 3-D printer (or additive manufacturing device) or using any other device through any other process can be designed and provided based on requirements of each specific individual subject or patient.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A biomechanically compatible implant for providing support to vaginal walls to treat vaginal walls prolapse, the biomechanically compatible implant comprising:
   a first flap configured to be attached to an anterior vaginal wall, wherein arbitrary selectable discrete locations of the first flap of the implant that is configured to contact the anterior vaginal wall are defined to exhibit biomechanical characteristics in accordance with biomechanical characteristics at arbitrary selectable discrete locations of the anterior vaginal wall where the respective arbitrary selectable discrete locations of the first flap are configured to be attached such that the biomechanical characteristics of the first flap that is configured to contact the anterior vaginal wall are different at arbitrary selectable discrete locations of the first flap of the implant, wherein the biomechanical characteristics of the first flap at the arbitrary selectable discrete locations are defined based on an input signifying age, pregnancy or childbirth state, intra-abdominal forces interactions, and state of prolapse associated with a subject;
   a second flap configured to be attached to a posterior vaginal wall, wherein arbitrary selectable discrete locations of the second flap of the implant that is configured to contact the posterior vaginal wall are defined to exhibit biomechanical characteristics in accordance with biomechanical characteristics at arbitrary selectable discrete locations of the posterior vaginal wall where the respective arbitrary selectable discrete locations of the second flap are configured to be attached such that the biomechanical characteristics of the second flap that is configured to contact the posterior vaginal wall are different at arbitrary selectable discrete locations of the second flap of the implant; and
   a third flap extending from the first flap and the second flap and configured to be attached to a tissue proximate sacrum.

2. The biomechanically compatible implant of claim 1, wherein number of arbitrary selectable discrete locations of the first flap is at least fifty such that the biomechanical characteristics at the arbitrary selectable at least fifty discrete locations of the first flap of the implant varies in accordance with variations in the biomechanical characteristics of the arbitrary selectable at least fifty discrete locations of the anterior vaginal wall.

3. The biomechanically compatible implant of claim 1, wherein number of arbitrary selectable discrete locations of the first flap is at least five such that the biomechanical characteristics at the arbitrary selectable at least five discrete locations of the first flap of the implant varies in accordance with variations in the biomechanical characteristics of the arbitrary selectable at least five discrete locations of the anterior vaginal wall.

4. The biomechanically compatible implant of claim 3, wherein at least one of the arbitrary selectable five discrete locations extends along a partial length of the first flap.

5. The biomechanically compatible implant of claim 3, wherein at least one of the arbitrary selectable five discrete locations extends along a partial width of the first flap.

6. The biomechanically compatible implant of claim 1, wherein number of arbitrary selectable discrete locations of the second flap is at least five such that the biomechanical characteristics at the arbitrary selectable at least five discrete locations of the second flap of the implant varies in accordance with variations in the biomechanical characteristics of the arbitrary selectable at least five discrete locations of the posterior vaginal wall.

7. The biomechanically compatible implant of claim 1, wherein the biomechanical characteristics at the arbitrary selectable discrete locations of the anterior vaginal wall are identified using a biomechanical pattern recognition device such that an input from the biomechanical pattern recognition device defines the biomechanical characteristics of the first flap at the arbitrary selectable discrete locations.

8. The biomechanically compatible implant of claim 1, wherein the biomechanical characteristics at the arbitrary selectable discrete locations of the first flap and the arbitrary selectable discrete locations of the second flap are determined from biomechanical characteristics patterns of the anterior vaginal wall and the posterior vaginal wall obtained from imaging of the anterior vaginal wall and the posterior vaginal wall at the arbitrary selectable locations of the first flap and the arbitrary selectable locations of the second flap respectively that are indicative of biomechanical characteristics gradients ranging along the entire anterior vaginal wall and the entire posterior vaginal wall.

9. The biomechanically compatible implant of claim 1, wherein the first flap, and the second flap are fabricated as mesh structures such that the biomechanical characteristics of the first flap and the second flap are defined differently by varying at least one of mesh parameters.

10. The biomechanically compatible implant of claim 9, wherein the mesh parameters comprise pore shape, pore construct, fabricating material, fabrication process, knit orientation, knit pattern, weave pattern, number of strands, number of pores per unit length, and number of pores per unit width.

11. A biomechanically compatible implant for providing support to vaginal walls to treat vaginal walls prolapse, the biomechanically compatible implant comprising:

a first flap configured to be attached to an anterior vaginal wall, wherein arbitrary selectable discrete locations of the first flap of the implant are defined to exhibit biomechanical characteristics in accordance with biomechanical characteristics at arbitrary selectable discrete locations of the anterior vaginal wall where the respective arbitrary selectable discrete locations of the first flap are configured to be attached, wherein the biomechanical characteristics of the first flap at the arbitrary selectable discrete locations are defined based on an input signifying age, pregnancy or childbirth state, intra-abdominal forces interactions, and state of prolapse associated with a subject;

a second flap configured to be attached to a posterior vaginal wall, wherein arbitrary selectable discrete locations of the second flap of the implant are defined to exhibit biomechanical characteristics in accordance with biomechanical characteristics at arbitrary selectable discrete locations of the posterior vaginal wall where the respective arbitrary selectable discrete locations of the second flap are configured to be attached;

a third flap extending from the first flap and the second flap and configured to be attached to a tissue proximate sacrum.

12. The biomechanically compatible implant of claim 11, wherein the biomechanical characteristics of the second flap at the arbitrary selectable discrete locations of the posterior vaginal wall are defined based on an input signifying age, pregnancy or childbirth state, intra-abdominal forces interactions, and state of prolapse associated with a subject.

* * * * *